(12) United States Patent
Cai et al.

(10) Patent No.: US 11,807,647 B2
(45) Date of Patent: Nov. 7, 2023

(54) CRYSTAL FORM OF HEPATITIS B SURFACE ANTIGEN INHIBITOR AND APPLICATION THEREOF

(71) Applicant: FUJIAN AKEYLINK BIOTECHNOLOGY CO., LTD., Fujian (CN)

(72) Inventors: Zhe Cai, Shanghai (CN); Fei Sun, Shanghai (CN); Charles Z. Ding, Shanghai (CN)

(73) Assignee: FUJIAN AKEYLINK BIOTECHNOLOGY CO., LTD., Fujian (CN)

( * ) Notice: Subject to any disclaimer, the term of this patent is extended or adjusted under 35 U.S.C. 154(b) by 12 days.

(21) Appl. No.: 17/760,818

(22) PCT Filed: Sep. 18, 2020

(86) PCT No.: PCT/CN2020/116051
§ 371 (c)(1),
(2) Date: Mar. 16, 2022

(87) PCT Pub. No.: WO2021/052447
PCT Pub. Date: Mar. 25, 2021

(65) Prior Publication Data
US 2022/0402939 A1 Dec. 22, 2022

(30) Foreign Application Priority Data
Sep. 19, 2019 (CN) .......................... 201910887908.1

(51) Int. Cl.
*C07D 498/04* (2006.01)
(52) U.S. Cl.
CPC ........ *C07D 498/04* (2013.01); *C07B 2200/13* (2013.01)
(58) Field of Classification Search
CPC ... C07D 498/04; C07B 2200/13; A61P 31/20; A61K 31/5365
See application file for complete search history.

(56) References Cited

U.S. PATENT DOCUMENTS

| 10,093,671 | B2 | 10/2018 | Han et al. |
| 11,008,331 | B2 | 5/2021 | Sun et al. |
| 2013/0251647 | A1 | 9/2013 | Subkowski et al. |
| 2019/0381014 | A1 | 12/2019 | Chen et al. |

FOREIGN PATENT DOCUMENTS

| CN | 107207505 A | 9/2017 |
| CN | 107759585 A | 3/2018 |
| CN | 108884107 A | 11/2018 |
| WO | 2018161960 A1 | 9/2018 |
| WO | 2019169539 A | 9/2019 |

OTHER PUBLICATIONS

Office Action dated Dec. 3, 2021 from Chinese Application No. 202010991558.6.
Notice of Allowance dated Mar. 30, 2022 from Chinese Application No. 202010991558.6.
Dec. 17, 2020 International Search Report issued in International Patent Application No. PCT/CN2020/116051.
Dec. 17, 2020 Written Opinion of the International Searching Authority issued in International Patent Application No. PCT/CN2020/116051.
Zhang Leihong et al., Crystallization and Recrystallization, Natural Medicinal Chemistry 3rd Edition, 31.1 Jan. 2017 (Jan. 31, 2017) pp. 23-24.
Fang Liang, Editor-in-Chief, Selection of Salt and Crystal Forms, Pharmacy 3rd Edition, Mar. 31, 2016 (Mar. 31, 2016) pp. 84-85.
First Office Action dated Jul. 11, 2023 issued in Japanese Patent Application No. 2022-517874.
Tirayama Yoshinaki, Handbook for organic compound crystal preparation—Principle and know-how, Marzen Co., Ltd., Jan. 25, 2008, p. 57-84.
Shozo Asahara, Solvent Handbook, 1985 (Table 3-3).

*Primary Examiner* — John M Mauro
(74) *Attorney, Agent, or Firm* — SZDC LAW P.C.

(57) ABSTRACT

Disclosed is a crystal form of a hepatitis B surface antigen inhibitor and a preparation method, and an application of the crystal form in the preparation of the hepatitis B surface antigen inhibitor.

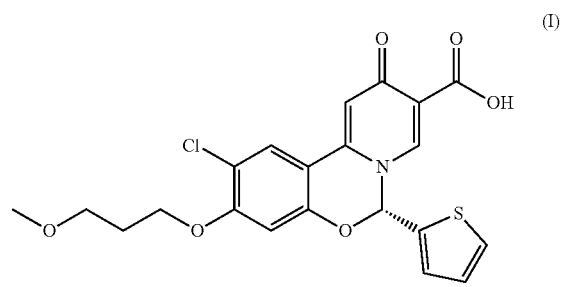

14 Claims, 2 Drawing Sheets
Specification includes a Sequence Listing.

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Forward primer

<400> SEQUENCE: 1
gtgtctgcgg cgttttatca                                                   20

<210> SEQ ID NO 2
<211> LENGTH: 21
<212> TYPE: DNA
<213> ORGANISM: Artificial Sequence
<220> FEATURE:
<223> OTHER INFORMATION: Reverse primer

<400> SEQUENCE: 2
gacaaacggg caacatacct t                                                 21
```

```
<210> SEQ ID NO 3
<211> LENGTH: 28
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..()
<223> OTHER INFORMATION: FAM at 5'-end
<220> FEATURE:
<221> NAME/KEY: misc_feature
<222> LOCATION: (28)..()
<223> OTHER INFORMATION: TAMRA at 3'-end

<400> SEQUENCE: 3
cctctkcatc ctgctgctat gcctcatc                                              28
```

CRYSTAL FORM OF HEPATITIS B SURFACE ANTIGEN INHIBITOR AND APPLICATION THEREOF

The present application is the National Stage Application of PCT/CN2020/116051, filed on Sep. 18, 2020, which claims the priority of Chinese patent application No. 201910887908.1, the application date of which is Sep. 19, 2019. This Chinese patent application is incorporated herein by reference in its entirety.

TECHNICAL FIELD

The present disclosure relates to a crystal form of a hepatitis B surface antigen inhibitor and a preparation method therefor, and further comprises an application of the crystal form in the preparation of the hepatitis B surface antigen inhibitor.

BACKGROUND

Viral hepatitis B, abbreviated as hepatitis B, is a disease caused by Hepatitis B Virus (abbreviated as HBV) infection in the body. Hepatitis B virus belongs to the hepadnaviridae family, mainly exists in liver cells and damages liver cells, causing inflammation, necrosis and fibrosis of hepatocytes. Viral hepatitis B is divided into two types, acute hepatitis B and chronic hepatitis B. Most adults with acute hepatitis B can heal themselves via their own immune mechanism. However, chronic hepatitis B (CHB) has become a great challenge to global health care, and a main cause of chronic liver disease, cirrhosis and hepatocellular carcinoma (HCC). It is estimated that 2 billion people worldwide are infected with chronic hepatitis B virus, more than 350 million people have developed hepatitis B, and nearly 600,000 people die each year from complications of chronic hepatitis B. China is a high-prevalence area of hepatitis B, with many accumulated patients with hepatitis B, which is a serious hazard. According to the data, there are about 93 million people infected with hepatitis B virus in China, and about 20 million of them are diagnosed with chronic hepatitis B, 10%-20% of which may develop into cirrhosis, and 1%-5% of which may develop into hepatocellular carcinoma.

The key to functional cure of hepatitis B is the clearance of HBsAg (hepatitis B surface antigen) and the production of surface antibodies. Quantification of HBsAg is a very important biological indicator. The reduction and seroconversion of HBsAg are rarely observed in patients with chronic infection, and are the endpoints of current therapies.

The surface antigen protein of hepatitis B virus (HBV) plays a very important role in the process of HBV invasion into hepatocytes, and is of great significance for the prevention and treatment of HBV infection. Surface antigen proteins include large (L), medium (M) and small (S) surface antigen proteins that share a common C-terminal S region. They are expressed from the same open reading frame and have different lengths that are defined by three AUG start codons in the reading frame. These three surface antigen proteins include pre-S1/pre-S2/S, pre-S2/S and S domains. HBV surface antigen protein is integrated into the endoplasmic reticulum (ER) membrane and is initiated by an N-terminal signal sequence. They not only constitute a basic structure of virions, but also form spherical and filamentous subviral particles (SVPs, HBsAg) that aggregate in the ER, host ER and pre-Golgi apparatus, and SVPs contain most of the S surface antigen proteins. L protein is critical in the morphogenesis of the virus and the interaction of nucleo-capsids, but is not necessary for the formation of SVP. Due to the absence of nucleocapsids, the SVPs are noninfectious. SVPs are greatly involved in disease progression, especially an immune response to hepatitis B virus. In the blood of infected people, the amount of SVPs is at least 10,000 times that of the virus, trapping the immune system and weakening the body's immune response to hepatitis B virus. HBsAg also can inhibit human innate immunity, polysaccharide (LPS) and IL-2-induced cytokine production, function of dendritic cells (DCs), and the induction activity of LPS against ERK-1/2 and c-Jun N-terminal interference kinase-1/2 in monocytes. Notably, progressions of cirrhosis and hepatocellular carcinoma are also largely associated with sustaining secretion of HBsAg. These findings suggest that HBsAg plays an important role in the development of chronic hepatitis.

The currently approved and marked anti-HBV drugs are mainly immunomodulators (interferon-α and peginterferon-α-2α) and antiviral drugs (lamivudine, adefovir dipivoxil, entecavir, telbivudine, tenofovir, clevudine, etc.). Among them, the antiviral drugs belong to nucleotide drugs, and their mechanism of action is to inhibit the synthesis of HBV DNA rather than directly reducing the level of HBsAg. As with the extended therapy, nucleotide drugs show HBsAg elimination at a rate similar to natural observations.

Existing clinical therapies have poor efficacy in reducing HBsAg. Therefore, the development of small molecule oral inhibitors that can effectively reduce HBsAg is urgently needed in current clinical medication.

Roche has developed a surface antigen inhibitor called RG7834 for the treatment of hepatitis B and reported the compound's efficacy in a woodchuck model against hepatitis B: when used as a single drug, RG7834 can reduce surface antigens by 2.57 Log and HBV-DNA by 1.7 Log. There is still a need for new compounds that can effectively reduce hepatitis B surface antigen, especially drugs for preventing or treating chronic hepatitis B.

CONTENT OF THE PRESENT INVENTION

The present disclosure provides a crystal form A of a compound of formula (I), wherein the crystal form has an X-ray powder diffraction pattern thereof comprising characteristic diffraction peaks at the following 2θ angles: 6.30±0.20°, 9.30±0.20°, and 20.16±0.20°;

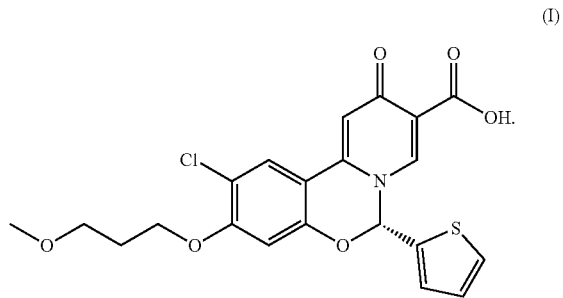 [SMILES: COCCCOc1cc2c(cc1Cl)-c1cc(=O)c(C(=O)O)cn1[C@H](c1cccs1)O2]

(I)

In some embodiments of the present disclosure, the above-mentioned crystal form A has an X-ray powder diffraction pattern comprising characteristic diffraction peaks at the following 2θ angles: 6.30±0.20°, 9.30±0.20°, 9.84±0.20°, 18.68±0.20°, 20.16±0.20°, 23.06±0.20°, 24.00±0.20°, and 25.38±0.20°.

In some embodiments of the present disclosure, the above-mentioned crystal form A has an X-ray powder diffraction pattern comprising characteristic diffraction peaks at the following 2θ angles: 6.30±0.20°, 9.30±0.20°, 9.84±0.20°, 12.84±0.20°, 18.68±0.20°, 20.16±0.20°, 21.26±0.20°, 23.06±0.20°, 24.00±0.20°, and 25.38±0.20°.

In some embodiments of the present disclosure, the above-mentioned crystal form A has an X-ray powder diffraction pattern comprising characteristic diffraction peaks at the following 2θ angles: 6.302°, 7.883°, 9.301°, 9.842°, 12.838°, 15.436°, 16.580°, 18.124°, 18.680°, 19.459°, 20.161°, 20.800°, 21.262°, 21.704°, 23.057°, 24.000°, 24.837°, 25.382°, 26.244°, 26.558°, 27.740°, 28.119°, 28.827°, 29.502°, 29.880°, 30.261°, 30.762°, 31.678°, 32.595°, 33.061°, 34.347°, 35.253°, 35.738°, 36.642°, 38.619°, and 39.558°.

In some embodiments of the present disclosure, the above-mentioned crystal form A has an XRPD pattern as shown in FIG. 1.

In some embodiments of the present disclosure, the above-mentioned crystal form A has an XRPD pattern analysis data as shown in Table 1:

TABLE 1

XRPD pattern analysis data of crystal form A of the compound of formula (I)

| No. | 2θ angle (°) | Interplanar spacing (Å) | Intensity | Relative intensity (%) |
|---|---|---|---|---|
| 1 | 6.302 | 14.0146 | 613 | 51.0 |
| 2 | 7.883 | 11.2067 | 222 | 18.5 |
| 3 | 9.301 | 9.5007 | 1202 | 100.0 |
| 4 | 9.842 | 8.9801 | 541 | 45.0 |
| 5 | 12.838 | 6.8901 | 434 | 36.1 |
| 6 | 15.436 | 5.7357 | 272 | 22.6 |
| 7 | 16.580 | 5.3424 | 253 | 21.0 |
| 8 | 18.124 | 4.8907 | 64 | 5.3 |
| 9 | 18.680 | 4.7463 | 650 | 54.1 |
| 10 | 19.459 | 4.5580 | 167 | 13.9 |
| 11 | 20.161 | 4.4009 | 978 | 81.3 |
| 12 | 20.800 | 4.2671 | 327 | 27.2 |
| 13 | 21.262 | 4.1755 | 397 | 33.0 |
| 14 | 21.704 | 4.0914 | 115 | 9.5 |
| 15 | 23.057 | 3.8542 | 854 | 71.0 |
| 16 | 24.000 | 3.7049 | 686 | 57.0 |
| 17 | 24.837 | 3.5819 | 158 | 13.2 |
| 18 | 25.382 | 3.5062 | 656 | 54.6 |
| 19 | 26.244 | 3.3930 | 96 | 8.0 |
| 20 | 26.558 | 3.3536 | 207 | 17.2 |
| 21 | 27.740 | 3.2133 | 315 | 26.2 |
| 22 | 28.119 | 3.1708 | 301 | 25.1 |
| 23 | 28.827 | 3.0946 | 57 | 4.8 |
| 24 | 29.502 | 3.0253 | 66 | 5.5 |
| 25 | 29.880 | 2.9878 | 225 | 18.7 |
| 26 | 30.261 | 2.9511 | 103 | 8.6 |
| 27 | 30.762 | 2.9041 | 71 | 5.9 |
| 28 | 31.678 | 2.8222 | 119 | 9.9 |
| 29 | 32.595 | 2.7449 | 54 | 4.5 |
| 30 | 33.061 | 2.7073 | 83 | 6.9 |
| 31 | 34.347 | 2.6088 | 49 | 4.1 |
| 32 | 35.235 | 2.5451 | 30 | 2.5 |
| 33 | 35.738 | 2.5104 | 75 | 6.2 |
| 34 | 36.642 | 2.4505 | 180 | 15.0 |
| 35 | 38.619 | 2.3295 | 55 | 4.6 |
| 36 | 39.558 | 2.2763 | 109 | 9.1 |

In some embodiments of the present disclosure, the above-mentioned crystal form A has a differential scanning calorimetry profile comprising an endothermic peak at 224.58° C.±3° C.

In some embodiments of the present disclosure, the above-mentioned crystal form A has a DSC pattern as shown in FIG. 2.

In some embodiments of the present disclosure, the above-mentioned crystal form A has a thermogravimetric analysis curve showing a weight loss of 0.127% at 200.00° C.±3° C. and a weight loss of 0.224% at 250° C.±3° C.

In some embodiments of the present disclosure, the above-mentioned crystal form A has a TGA pattern as shown in FIG. 3.

The present disclosure provides a preparation method of the crystal form A of the compound of formula (I), wherein the method comprises adding the compound of formula (I) in any form to an alcohol solvent, acetone, ethyl acetate, acetonitrile, or an alcohol solvent, acetone, acetonitrile and water, stirring the mixture for a given time at a given temperature, then filtering, and drying a filter cake to obtain the crystal form A.

In some embodiments of the present disclosure, the volume ratio of the above-mentioned alcohol solvent, acetone, acetonitrile and water is selected from 1:5-3.

In some embodiments of the present disclosure, the volume ratio of the above-mentioned alcohol solvent, acetone, acetonitrile and water is selected from 1:1-3.

In some embodiments of the present disclosure, the above-mentioned alcohol solvent is selected from methanol, ethanol or isopropanol.

In some embodiments of the present disclosure, stirring is performed at a temperature selected from 25° C. to 65° C.

In some embodiments of the present disclosure, stirring is performed for a time period selected from 1 hour to 72 hours.

In some embodiments of the present disclosure, the weight ratio of the above-mentioned compound of formula (I) to the solvent is selected from 1:1-30.

In some embodiments of the present disclosure, the weight ratio of the above-mentioned compound of formula (I) to the solvent is selected from 1:5-30.

The present disclosure further provides use of the above-mentioned compound of formula (I) or the above-mentioned crystal form A of the compound of formula (I) in the preparation of a drug for treating chronic hepatitis B.

Technical Effects

The compound of the present disclosure has significant anti-hepatitis B virus activity. The compound of the present disclosure does not inhibit cytochrome P450 isoenzymes, indicating a lower risk of drug-drug interactions; has excellent stability of liver microsomes in three species, i.e., rat, human and mouse, indicating that the compound is not easily metabolized; has better exposure and bioavailability; and is well tolerated in a single-dose neurotoxicity study.

The crystal form A of the compound of the present disclosure is easy to obtain, has good physical stability and chemical stability, and has high industrial application value and economic value.

Definition and Description

Unless otherwise stated, the following terms and phrases used herein are intended to have the following meanings. A specific phrase or term should not be considered uncertain or unclear unless specifically defined, but should be understood in an ordinary meaning. When a trade name appears herein, it is intended to refer to the corresponding commodity or an active ingredient thereof.

The intermediate compounds of the present disclosure can be prepared by various synthetic methods well known to a person skilled in the art, including the specific embodiments listed below, the embodiments formed by the combination with other chemical synthesis methods, and equivalent alternative embodiments well known to a person skilled in the art, wherein the preferred embodiments include but are not limited to the examples of the present disclosure.

The chemical reactions described in the specific embodiments of the present disclosure are completed in a suitable solvent, wherein the solvent must be suitable for the chemical changes of the present disclosure and the reagents and materials required thereby. In order to obtain the compounds of the present disclosure, sometimes a person skilled in the art needs to modify or select synthesis steps or reaction schemes based on the existing embodiments.

The present disclosure will be specifically described below by way of examples which are not intended to limit the present disclosure in any way.

All solvents used in the present disclosure are commercially available and can be used without further purification.

Compounds are named by hand or ChemDraw® software, and commercially available compounds are named by the supplier catalog names.

The X-Ray Powder Diffractometer (XRPD) Method Used in the Present Disclosure
  Instrument model: Dandong Haoyuan DX-2700BH X-ray diffractometer
  Test method: approximately 10 mg to 20 mg of the sample is used for XRPD detection.
  The detailed XRPD parameters are as follows:
  Light tube: Cu, kα, (λ=1.54184 Å).
  Light tube voltage: 40 kV, light tube current: 30 mA
  Divergence slit: 1 mm
  Detector slit: 0.3 mm
  Anti-scatter slit: 1 mm
  Scanning range: 3-40 deg
  Step size: 0.02 deg
  Step length: 0.5 sec
The Differential Scanning Calorimeter (DSC) Method Used in the Present Disclosure
  Instrument model: METTLER TOLEDO DSC1 Differential Scanning calorimeter
  Test method: the sample (2-6 mg) was placed in a 30 UL DSC gold-plated high pressure crucible for test, and heated from 40° C. to 350° C. at a heating rate of 10° C./min.
The Thermal Gravimetric Analyzer (TGA) Method Used in the Present Disclosure
  Instrument model: TA TGA550 Thermogravimetric Analyzer
  Test method: the sample (2-10 mg) was placed in an aluminum crucible, then placed in a platinum hanging basket for test, and heated from 40° C. to 500° C. under nitrogen ($N_2$) conditions at a gas flow rate of 40 mL/min and a heating rate of 10° C./min.

DETAILED DESCRIPTION OF THE PREFERRED EMBODIMENT

Figure 1:
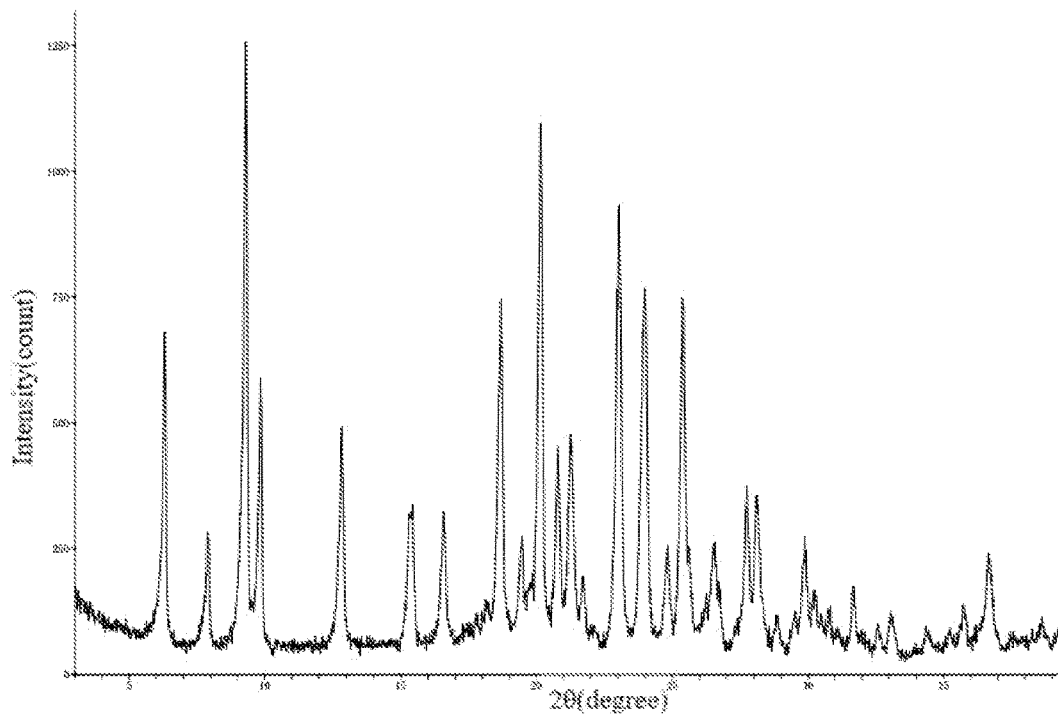
FIG. 1 is an XRPD pattern of Cu-Kα radiation of crystal form A of the compound of formula (I).

In order to better understand the content of the present disclosure, the following specific examples are used for further description, but the specific embodiments do not limit the content of the present disclosure.

Example 1: Preparation of a Compound of Formula (I)

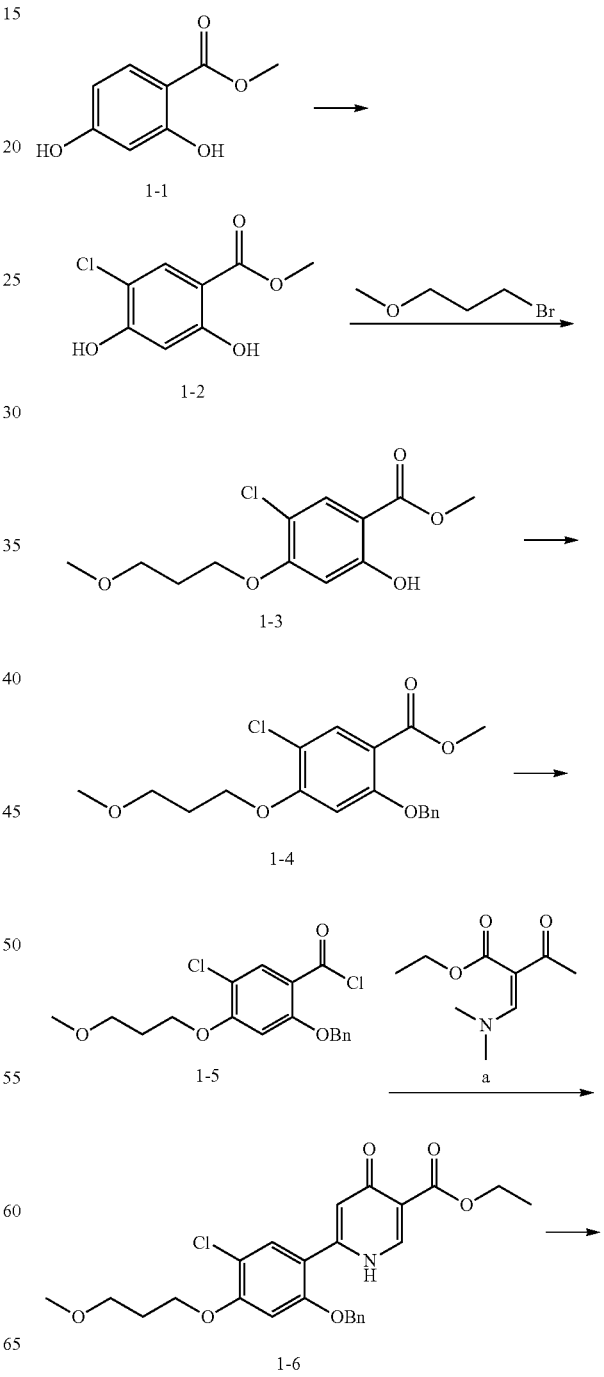

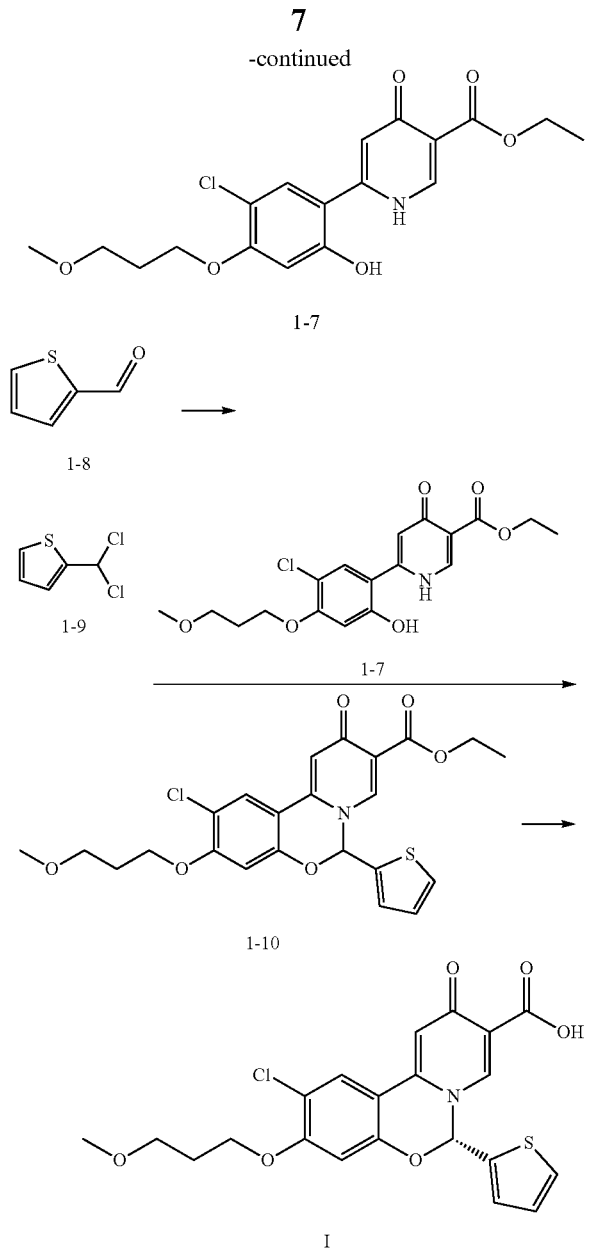

Step A: 1-1 (10.00 g, 59.5 mmol) was dissolved in dichloromethane (500 mL) at 0° C., and then sulfonyl chloride (10.77 g, 79.77 mmol, 7.98 mL) was added; and the mixed solution was stirred at 35° C. for 38 hours. The solution was then poured into 300 mL of saturated aqueous sodium bicarbonate solution, stirred and separated. The aqueous phase was extracted with ethyl acetate (150 mL×3), and then the combined organic phases were washed with saturated brine (40 mL×3), dried over anhydrous sodium sulfate, and distilled under reduced pressure to obtain a white residue. The white residue was then purified by silica gel column chromatography (eluent: petroleum ether/ethyl acetate=30/1 to 20/1) to obtain compound 1-2.

$^1$H NMR (400 MHz, MeOH-d$_4$) δ 10.75 (s, 1H), 7.74 (s, 1H), 6.54 (s, 1H), 5.98 (s, 1H), 3.85 (s, 3H).

Step B: 1-2 (8.00 g, 39.49 mmol), and 1-bromo-3-methoxy-propane (7.25 g, 47.39 mmol) were dissolved in N,N-dimethylformamide (100.00 mL) and cooled to 0° C. Then potassium carbonate (10.92 g, 78.98 mmol) was added, and the mixed solution was warmed to 25° C. and stirred for 10 hours. Ethyl acetate (300 mL) and water (50 mL) were added to the solution, and the resulting solution was stirred at 25° C. for 10 minutes. The organic phase was separated and washed with saturated brine (40 mL×3), then dried over anhydrous sodium sulfate, and concentrated under reduced pressure to obtain a yellow liquid. The yellow liquid was purified by silica gel column chromatography (eluent: petroleum ether/ethyl acetate=30/1 to 20/1) to obtain compound 1-3.

$^1$H NMR (400 MHz, CDCl$_3$) δ 10.90 (s, 1H), 7.82 (s, 1H), 6.52 (s, 1H), 4.16 (t, J=6.0 Hz, 2H), 3.94 (s, 3H), 3.60 (t, J=6.0 Hz, 2H), 3.38 (s, 3H), 2.13 (t, J=6.0 Hz, 2H).

Step C: To a solution of 1-3 (3.64 g, 13.25 mmol) and benzyl chloride (2.18 g, 17.23 mmol, 1.98 mL) in N,N-dimethylformamide (10.00 mL), potassium carbonate (4.76 g, 34.45 mmol) was added, and the mixed solution was stirred at 25° C. for 20 hours. Ethyl acetate (150 mL) and water (30 mL) were added to the solution, and the resulting solution was stirred at 20° C. for 10 minutes. The organic phase was then separated and washed with water (30 mL×2) and saturated brine (30 mL×2), then dried over anhydrous sodium sulfate, and concentrated under reduced pressure to obtain compound 1-4.

Step D: 1-4 (2.00 g, 5.48 mmol) and lithium hydroxide monohydrate (1.38 g, 32.89 mmol) were added to a mixed solution of tetrahydrofuran (20 mL) and water (10 mL), and then the resulting solution was stirred at 10° C. to 20° C. for 10 hours. The solution was then washed with ethyl acetate/petroleum ether 1/1 (5 mL×3). The water phase was adjusted to pH 1 to 2. The solution was then extracted with dichloromethane (50 mL×3), and the organic phases were combined, dried over anhydrous sodium sulfate, and concentrated under reduced pressure to obtain compound 2-benzyloxy-5-chloro-4-(3-methoxylpropane) benzoic acid. To a solution of 2-benzyloxy-5-chloro-4-(3-methoxypropane) benzoic acid formic acid (1.00 g, 2.85 mmol) in dichloromethane (10.00 mL), thionyl chloride (508.60 mg, 4.28 mmol, 310.12 μl) was added, and the mixed solution was stirred at 25° C. for 1 hour. The solution was then concentrated under reduced pressure to give a residue. The residue was dissolved in toluene and concentrated under reduced pressure to obtain a residue, and residue 1-5 was stored under nitrogen atmosphere.

$^1$H NMR (400 MHz, DMSO-d$_6$) δ 12.87-12.22 (m, 1H), 7.74 (s, 1H), 7.53 (br d, J=7.2 Hz, 2H), 7.40 (t, J=7.6 Hz, 2H), 7.36-7.30 (m, 1H), 6.94 (s, 1H), 5.27 (s, 2H), 4.20 (s, 2H), 3.50 (s, 2H), 3.26 (s, 3H), 1.98 (t, J=6.4 Hz, 2H).

Step E: A solution of 1-5 (2.94 g, 7.96 mmol) and compound a (1.62 g, 8.76 mmol, 1.10 eq) in tetrahydrofuran (20 mL) was added dropwise (5 min) to a solution of lithium hexamethyldisilazide (1 mol/L, 23.88 mL) in tetrahydrofuran (20 mL) at −70° C. Then a cooling bath was removed, and the mixture was allowed to continue stirring for 5 minutes. Ammonium acetate (3.23 g, 41.95 mmol) and acetic acid (67.85 g, 1.13 mmol) were added to the mixture, and most of the tetrahydrofuran was removed by rotary evaporator at 60° C., and the residue was heated at 60° C. to 65° C. for 1.5 hours. The reaction mixture was cooled, and then water (40 mL) and dichloromethane (200 mL) were added thereto. The mixture was stirred for 10 minutes and separated, and the organic phase was washed with water (10 mL×3) and aqueous sodium bicarbonate solution, dried, and concentrated to obtain a yellow residue. The residue was purified by silica gel column chromatography (eluent: petroleum ether/ethyl acetate=10/1) to obtain compound 1-6.

Step F: To a solution of 1-6 (3.00 g, 6.36 mmol) in tetrahydrofuran (20 mL), palladium on activated carbon (wet) (500 mg) was added, and the solution was stirred at 25° C. for 2 hours under an atmosphere of hydrogen (15 psi). The brown suspension was then filtered, and the filtrate was collected and concentrated under reduced pressure to obtain a residue. The residue was then slurried with petroleum ether/ethyl acetate (4/1) (twice) and filtered to obtain compound 1-7.

Step G: To a solution of 1-8 (20.00 g, 178.33 mmol) in dichloromethane (150.00 mL), pyridine (2.82 g, 35.67 mmol) followed by phosphorus pentachloride (37.14 g, 178.33 mmol) was added at −10° C., and the resulting mixture was reacted at −10° C. for 0.5 hour. After the reaction was completed, sodium bicarbonate (44.94 g, 534.99 mmol) was added to the reaction system. The reaction was stirred for another 0.5 hours, then filtered through celite and washed with dichloromethane (20 mL×3), and the filtrate was concentrated to obtain residue 1-9.

$^1$H NMR (400 MHz, CDCl$_3$) δ 7.68 (d, J=3.91 Hz, 1H), 7.35-7.44 (m, 5H), 7.22 (d, J=3.67 Hz, 1H), 6.91 (s, 1H), 5.34 (s, 2H).

Step H: a solution of 1-7 (10.00 g, 26.19 mmol), cesium carbonate (38.40 g, 117.86 mmol) and 1-9 (21.88 g, 130.95 mmol) in dimethyl sulfoxide (100.00 mL) was stirred at 100° C. for 16 hours. After the reaction was completed, the reaction was quenched with 50 mL of water. The reaction solution was diluted with 150 mL of water and extracted with dichloromethane (100 mL×3). Then the organic phases were combined, washed with saturated brine (100 mL×3), dried over anhydrous sodium sulfate, and concentrated under reduced pressure to obtain a residue. The residue was purified by silica gel column chromatography (eluent: dichloromethane/ethanol=100/1 to 8/1) to obtain compound 1-10.

Step I: 1-10 was separated by chiral chromatography column (separation column: AS (250 mm×30 mm, 10 μm); mobile phase: [0.1% ammonia water-ethanol]; elution gradient: 40%-40%, 4.3 min; 120 min) to obtain two configurational isomers, with retention time=2.516 min and 5.098 min, respectively. The isomer with retention time=2.516 min (55 mg, 116.64 μmol) was then placed in a solution of methanol (10 mL), and 4 mol/ml sodium hydroxide (145.80 μL) was added. The reaction solution was stirred at 25° C. to 30° C. for 2 hours. The reaction solution was concentrated under reduced pressure; the residue was dissolved in water (20 mL) and adjusted to pH 1 to 2 with 2 mol/l hydrochloric acid; a solid was precipitated and then filtered and dried to obtain a compound of formula (I) (retention time=3.842 min), ee value (enantiomeric excess): 100%. Method for measuring ee values (enantiomeric excess): OD-3S_3_40_3 ML Separation column: Chiralcel OD-3 100×4.6 mm I.D., 3 μm Mobile phase: 40% methanol (0.05% diethylamine) in CO$_2$, flow rate: 3 mL/min wavelength: 220 nm.

Compound of formula (I): $^1$H NMR (400 MHz, CDCl$_3$) δ 15.40 (s, 1H), 8.32 (s, 1H), 7.62 (s, 1H), 7.41 (dd, J=1.28, 4.83 Hz, 1H), 6.93-6.98 (m, 2H), 6.91 (s, 1H), 6.88 (s, 1H), 6.62 (s, 1H), 4.09 (t, J=6.24 Hz, 2H), 3.51 (t, J=5.87 Hz, 2H), 3.28 (s, 3H), 2.05 (quin, J=6.08 Hz, 2H).

Example 2: Preparation of Crystal Form A of the Compound of Formula (I)

With temperature controlled at 40° C., the compound of formula (I) (1 g) was added to a reaction flask, and then acetone (10 mL) was added. The mixture was stirred at 40° C. for 24 hours, cooled to room temperature and filtered, and the filter cake was washed with acetone (10 mL) to obtain a crude, which was dried in a vacuum drying oven (45° C., 16 hours) to obtain crystal form A of the compound of formula (I).

Example 3: Stability Test of Crystal Form A of the Compound of Formula (I), as a Solid, Under High Temperature and High Humidity Conditions 2 samples of crystal form A of the compound of formula (I) were weighed in parallel (about 100 mg each), placed on the bottom of glass sample bottles, and spread out as a thin layer. The bottles were sealed with aluminum foil paper, and some small holes were made on the aluminum foil paper to ensure that the samples could fully contact with ambient air. The bottles were placed in a constant temperature and humidity chamber at 40° C./75% humidity. The samples placed under the above-mentioned conditions were sampled and tested on day 5 and day 10. The test results were compared with initial test results on day 0. The test results are shown in Table 2 below:

TABLE 2

Stability test of crystal form A, as a solid, under high temperature and high humidity conditions

| Time point (day) | Appearance | Polymorph | Purity (%) | Total impurities (%) |
|---|---|---|---|---|
| 0 | White powder | Polymorph A | 99.79 | 0.21 |
| 5 | White powder | Polymorph A | 99.79 | 0.21 |
| 10 | White powder | Polymorph A | 99.79 | 0.21 |

Experimental conclusion: the crystal form A of the compound of the formula (I) in the present disclosure has good stability and is easy to be formulated into a medicine.

Example 4: Physical Stability Test of Crystal Form A of the Compound of Formula (I), as a Solid, Under Various Temperature, Humidity and Light Conditions 4 samples of crystal form A of the compound of formula (I) were weighed in parallel (about 100 mg each), placed on the bottom of glass sample bottles, and spread out as a thin layer. The bottles were sealed with aluminum foil paper, and some small holes were made on the aluminum foil paper to ensure that the samples could fully contact with ambient air. The prepared 4 samples were placed under a relative humidity of 25° C./92.5%, 60° C., 40° C./75% and light conditions, respectively, to investigate the physical stability of the samples on day 10. In addition, about 100 mg of crystal form A solid of the compound of formula (I) was separately weighed, placed at the bottom of a glass sample bottle, sealed with a screw cap and stored at −20° C. for use as a control sample. On day 10, all samples were taken out, returned to room temperature, and observed for appearance changes, and the crystal forms of the samples were detected by XRPD. By comparing an accelerated sample with the control sample, the physical stability of crystal form A of the compound of formula (I), as a solid, was determined. Table 3 below shows experimental results of physical stability of the crystal form A as a solid.

TABLE 3

Physical stability test of crystal form A, as a solid, under various temperature, humidity and light conditions

| Investigated item | Time point | Day 0 (−20° C. storage with seal) (control sample) | 25° C./92.5% Relative humidity (open) | 60° C. (open) | 40° C./75% Relative humidity (open) | Light |
|---|---|---|---|---|---|---|
| Polymorph | Day 10 | Polymorph A | Polymorph A | Polymorph A | Polymorph A | Polymorph A |
| Character | Day 10 | White powder | White powder | White powder | White powder | White powder |
| Purity (%) | Day 10 | 99.79 | 99.80 | 99.75 | 99.79 | 99.71 |

Experimental conclusion: The crystal form A of the compound of the formula (I) in the present disclosure has good stability and is easy to be formulated into a medicine.

Example 5: Single Crystal X-Ray Diffraction Analysis

It is not easy to cultivate a single crystal for the compound of formula (I), and in order to confirm its absolute configuration, the compound of formula (I) is methylated with trimethylsilyldiazomethane to obtain a compound of formula (II), and then a single crystal for compound of formula (II) is cultivated.

The preparation method was as follows:

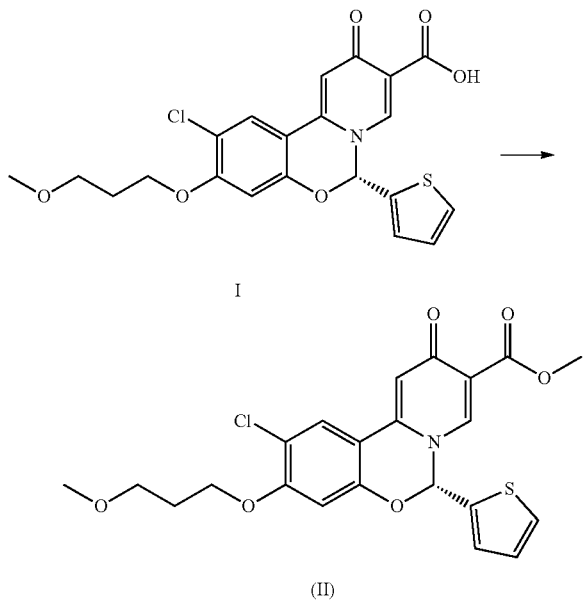

the compound of formula (I) (5 g, 11.16 mmol) was added to a mixed solution of methanol (15 mL) and tetrahydrofuran (45 mL), and trimethylsilyldiazomethane (2 mol/L, 8.37 mL) was added in one portion at room temperature. Then the resulting solution was stirred at room temperature for 12 hours. The reaction solution was concentrated, and then 20 ml of tert-butyl methyl ether was added; and the resulting solution was stirred, filtered and dried to obtain the compound of formula (II). The compound of formula (II) was dissolved in methanol, and the resulting solution was cultured at room temperature for 10 days using the solvent evaporation method to obtain a single crystal of the compound of formula (II), with a crystal size for diffraction of 0.06×0.08×0.16 mm. The crystal belongs to a triclinic system, with space group P1, crystal cell parameters: a=13.0669(13), b=13.4585(12), c=14.4699(14)Å, α=90.348(4), β=109.374(4), γ=96.367(4), crystal cell volume V=2383.3(4)Å3, the number of asymmetric units in the crystal cell Z=1.

Diffraction intensity data was collected with Bruker D8 venture diffractometer, with CuKα radiation as a light source and φ/ω scanning as a scanning mode, wherein the number of total diffraction points collected was 40999, the number of independent diffraction points was 15341, and the number of observable points (I/sigma≥2) was 5471.

The crystal structure was analyzed by the direct method (Shelxs97) to obtain 124 non-hydrogen atom positions. The least squares method was used to correct structural parameters and identify the atomic species. The geometric calculation method and the difference Fourier method were used to obtain all hydrogen atom positions. After refinement, $R_1=0.1357$, $wR_2=0.4252$ ($w=1/\alpha|F|^2$), S=1.817. The final stoichiometric formula was $4(C_{22}H_{20}ClNO_6S)$; the calculated single molecular weight was 461.90; and the calculated crystal density was 1.287 g/cm$^3$.

Figure 4:
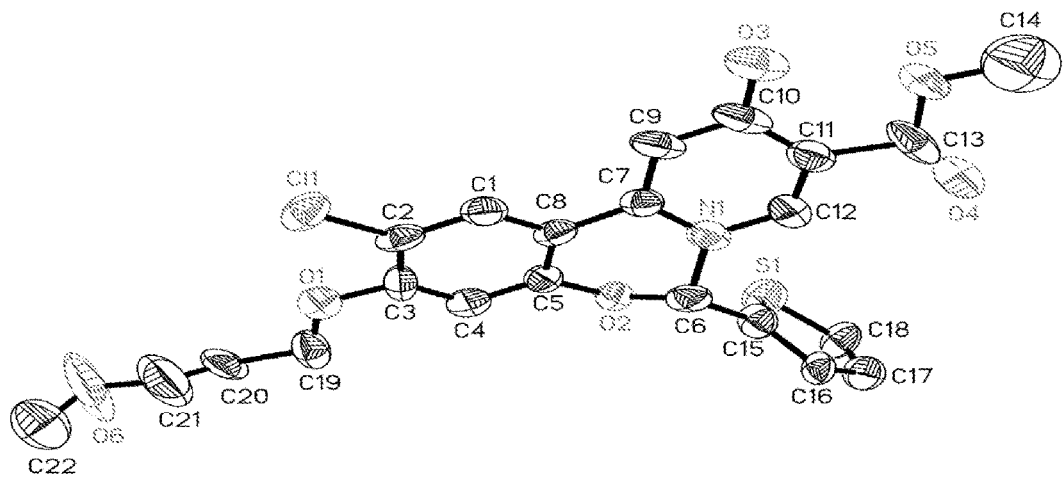
FIG. 4 is an ellipsoid diagram of single crystal X-ray diffraction for stereochemical structure of the compound of formula (II).

The reaction was carried out in a neutral environment with mild conditions, without inversion at a chiral carbon. Therefore, the absolute configuration of the compound of formula (I) was consistent with that of the compound of formula (II). From the single crystal data of the compound of formula (II), the absolute configuration of the compound of formula (I) can be determined. The ellipsoid diagram for monomolecular stereochemical structure of the compound of formula (II) was shown in FIG. 4. See Table 4 for atomic coordinates (×10$^4$) and equivalent isotropic displacement parameters (Å$^2$×10$^3$) of the crystal of the compound of formula (II). See Table 5 for bond length (Å) and bond angle [deg] of the compound of formula (II). See Table 6 for Twist angle [deg] of the compound of formula (II).

TABLE 4

Atomic coordinates (×10$^4$) and equivalent isotropic displacement parameters (Å$^2$ × 10$^3$) of the crystal of the compound of formula (II)

| | x | y | z | U(eq) |
|---|---|---|---|---|
| Cl(1) | −5132(6) | 7567(4) | 1373(5) | 110(2) |
| Cl(2) | 6227(6) | 2481(4) | 4348(5) | 117(2) |
| Cl(3) | 4871(6) | 7558(4) | 6373(5) | 111(2) |
| Cl(4) | −3762(6) | 2481(4) | −653(5) | 115(2) |
| S(1) | −5696(6) | 1040(5) | 343(5) | 114(2) |
| S(2) | 6789(6) | 8996(5) | 3561(5) | 111(2) |
| S(3) | 4294(6) | 1034(5) | 5343(5) | 116(2) |
| S(4) | −3211(6) | 8991(5) | −1439(5) | 114(2) |
| O(1) | −7185(15) | 6424(12) | 378(14) | 113(5) |
| O(1') | −1935(18) | 7130(20) | 1900(30) | 229(16) |
| O(2) | −5885(10) | 3214(9) | 844(10) | 76(4) |
| O(2') | −252(15) | 5983(19) | 1814(17) | 164(8) |
| O(3) | −862(15) | 4102(16) | 2377(15) | 132(7) |
| O(3') | 1441(14) | 3930(20) | 3151(18) | 174(10) |
| O(4) | −1920(30) | 930(20) | 2470(30) | 165(11) |

TABLE 4-continued

Atomic coordinates (×10$^4$) and equivalent isotropic displacement parameters (Å$^2$ × 10$^3$) of the crystal of the compound of formula (II)

| | x | y | z | U(eq) |
|---|---|---|---|---|
| O(4') | 3000(18) | 2905(19) | 2890(20) | 216(14) |
| O(5') | 8061(17) | 7140(20) | 6910(20) | 215(14) |
| O(5) | −489(19) | 2110(20) | 2500(20) | 190(14) |
| O(6') | 9741(14) | 5981(18) | 6858(16) | 151(7) |
| O(6) | −9850(40) | 8180(30) | −430(30) | 360(30) |
| O(7) | 8342(18) | 3625(11) | 4729(14) | 127(6) |
| O(7') | 11433(15) | 3930(20) | 8155(19) | 206(11) |
| O(8) | 7007(10) | 6823(10) | 4199(10) | 78(4) |
| O(8') | 13003(18) | 2873(18) | 7880(20) | 208(13) |
| O(9) | 1927(13) | 5900(20) | 2588(15) | 150(9) |
| O(10) | 1552(16) | 7951(16) | 2559(17) | 156(9) |
| O(11) | 2899(17) | 8900(20) | 3351(16) | 145(8) |
| O(13) | 2767(14) | 6425(10) | 5344(12) | 99(5) |
| O(14) | 4126(11) | 3191(10) | 5870(10) | 86(4) |
| O(15) | 9167(16) | 4090(20) | 7397(15) | 137(7) |
| O(16) | 9490(20) | 2100(20) | 7510(20) | 193(12) |
| O(17) | 8090(20) | 950(20) | 7440(30) | 164(12) |
| O(18) | 310(50) | 8280(30) | 4650(30) | 300(30) |
| O(19) | −1768(16) | 3632(11) | −309(14) | 118(5) |
| O(20) | −2994(11) | 6845(9) | −786(10) | 81(4) |
| O(21) | −8059(13) | 5913(18) | −2396(13) | 134(7) |
| O(22) | −8448(16) | 7930(19) | −2424(18) | 156(9) |
| O(23) | −7100(20) | 8920(30) | −1636(16) | 149(12) |
| N(1) | −4050(14) | 3042(13) | 1759(12) | 81(5) |
| N(2) | 5141(13) | 7003(14) | 3969(12) | 78(5) |
| N(3) | 5940(13) | 3050(12) | 6764(12) | 75(5) |
| N(4) | −4837(13) | 6998(13) | −1016(11) | 73(4) |
| C(1) | −4460(20) | 5715(16) | 1584(17) | 84(6) |
| C(2) | −5358(19) | 6302(15) | 1215(17) | 82(7) |
| C(3) | −6381(19) | 5788(15) | 743(16) | 87(7) |
| C(4) | −6594(18) | 4796(16) | 602(16) | 82(6) |
| C(5) | −5736(17) | 4262(14) | 972(16) | 73(6) |
| C(6) | −5241(19) | 2717(15) | 1629(16) | 83(6) |
| C(7) | −3738(17) | 4058(16) | 1742(15) | 75(6) |
| C(8) | −4671(17) | 4684(14) | 1435(15) | 76(5) |
| C(9) | −2664(19) | 4400(19) | 1937(18) | 101(8) |
| C(10) | −1850(20) | 3760(30) | 2180(20) | 113(9) |
| C(11) | −2220(20) | 2680(20) | 2174(18) | 103(8) |
| C(12) | −3263(19) | 2408(17) | 2004(15) | 84(6) |
| C(13) | −1560(40) | 1670(40) | 2330(30) | 140(10) |
| C(14) | 200(60) | 1210(50) | 2640(50) | 270(30) |
| C(15) | −5515(18) | 1598(13) | 1455(16) | 88(7) |
| C(16) | −5713(16) | 912(12) | 2196(17) | 77(6) |
| C(17) | −5980(20) | −72(17) | 1650(20) | 104(8) |
| C(18) | −5980(20) | −61(15) | 760(20) | 103(8) |
| C(19) | −8210(20) | 6070(20) | 64(17) | 109(10) |
| C(20) | −9020(20) | 6810(30) | −390(30) | 166(16) |
| C(21) | −9160(40) | 7530(40) | 90(30) | 240(30) |
| C(22) | −10350(30) | 8580(40) | −30(40) | 250(30) |
| C(23) | 5606(19) | 4307(16) | 4099(13) | 82(6) |
| C(24) | 6450(20) | 3780(16) | 4295(15) | 80(6) |
| C(25) | 7480(20) | 4178(17) | 4473(15) | 93(7) |
| C(26) | 7663(18) | 5240(16) | 4444(16) | 84(6) |
| C(27) | 6808(17) | 5803(14) | 4260(16) | 74(5) |
| C(28) | 6299(16) | 7351(14) | 4556(15) | 76(5) |
| C(29) | 4877(19) | 5987(18) | 3782(16) | 83(6) |
| C(30) | 5728(18) | 5365(17) | 4046(15) | 79(6) |
| C(31) | 3860(20) | 5640(20) | 3320(20) | 98(8) |
| C(32) | 2950(30) | 6210(20) | 3026(19) | 122(11) |
| C(33) | 3256(17) | 7260(30) | 3254(17) | 110(10) |
| C(34) | 4370(20) | 7650(30) | 3747(19) | 90(7) |
| C(35) | 2470(30) | 7970(20) | 3010(20) | 117(11) |
| C(36) | 2130(30) | 9580(30) | 3030(40) | 220(30) |
| C(37) | 6655(17) | 8416(14) | 4537(17) | 89(6) |
| C(38) | 6862(16) | 9157(14) | 5391(18) | 81(6) |
| C(39) | 7120(20) | 10130(18) | 5033(19) | 117(10) |
| C(40) | 7110(20) | 10107(19) | 4130(20) | 106(8) |
| C(41) | 9520(20) | 4000(20) | 5060(20) | 111(9) |
| C(42) | 10030(50) | 2800(40) | 5280(20) | 270(20) |
| C(45) | 5530(19) | 5731(16) | 6584(15) | 88(6) |
| C(46) | 4630(20) | 6243(13) | 6206(17) | 88(7) |
| C(47) | 3540(20) | 5804(18) | 5694(17) | 86(7) |
| C(48) | 3422(19) | 4783(16) | 5616(15) | 88(6) |
| C(49) | 4302(17) | 4218(15) | 5988(15) | 76(6) |
| C(50) | 4764(16) | 2715(14) | 6688(17) | 82(6) |
| C(51) | 6243(17) | 4071(14) | 6745(14) | 73(5) |
| C(52) | 5329(19) | 4702(17) | 6443(16) | 79(6) |
| C(53) | 7321(19) | 4390(20) | 6925(16) | 97(7) |
| C(54) | 8170(20) | 3790(20) | 7159(18) | 104(8) |
| C(55) | 7760(20) | 2690(20) | 7165(18) | 100(9) |
| C(56) | 6713(18) | 2388(17) | 6983(17) | 91(7) |
| C(57) | 8410(30) | 1730(40) | 7400(20) | 162(19) |
| C(58) | 10160(50) | 1260(40) | 7400(50) | 540(60) |
| C(59) | 4492(18) | 1626(18) | 6444(16) | 92(7) |
| C(60) | 4272(16) | 929(13) | 7181(17) | 81(6) |
| C(61) | 4040(30) | −79(19) | 6670(20) | 118(9) |
| C(62) | 4050(20) | −79(17) | 5750(20) | 118(9) |
| C(63) | 1662(19) | 5956(19) | 5048(19) | 103(7) |
| C(64) | 880(30) | 6770(20) | 4580(20) | 138(11) |
| C(65) | 980(40) | 7580(30) | 5130(30) | 220(20) |
| C(66) | −350(30) | 8550(40) | 4960(40) | 200(20) |
| C(67) | −4417(19) | 4312(15) | −921(14) | 77(6) |
| C(68) | −3580(20) | 3778(14) | −729(15) | 80(6) |
| C(69) | −2550(20) | 4235(17) | −512(16) | 92(7) |
| C(70) | −2332(17) | 5295(13) | −554(16) | 84(7) |
| C(71) | −3210(17) | 5828(16) | −762(16) | 81(6) |
| C(72) | −3670(17) | 7353(15) | −410(17) | 86(7) |
| C(73) | −5137(18) | 5977(15) | −1221(14) | 73(6) |
| C(74) | −4288(16) | 5359(14) | −950(15) | 70(5) |
| C(75) | −6193(18) | 5650(20) | −1699(15) | 96(7) |
| C(76) | −7050(20) | 6300(30) | −1968(19) | 109(11) |
| C(77) | −6700(20) | 7370(20) | −1722(17) | 93(7) |
| C(78) | −5584(19) | 7637(19) | −1240(15) | 87(6) |
| C(79) | −7510(30) | 8010(30) | −2040(30) | 139(17) |
| C(80) | −7880(20) | 9610(30) | −1960(40) | 230(30) |
| C(81) | −3339(17) | 8440(17) | −460(15) | 82(6) |
| C(82) | −3144(16) | 9142(14) | 412(15) | 79(6) |
| C(83) | −2890(30) | 10120(20) | −10(20) | 132(12) |
| C(84) | −2910(20) | 10130(20) | −890(30) | 112(9) |
| C(85) | −660(20) | 4080(20) | −90(20) | 130(10) |
| C(86) | 270(60) | 3700(50) | 640(50) | 390(40) |
| C(88) | 1700(50) | 1330(50) | 400(40) | 530(30) |
| O(24) | 140(50) | 1500(40) | 360(40) | 511(17) |
| C(87) | −310(40) | 2930(40) | −50(40) | 331(19) |
| H(1A) | −3762 | 6021 | 1916 | 101 |
| H(4A) | −7294 | 4485 | 267 | 98 |
| H(6A) | −5380 | 2915 | 2226 | 100 |
| H(9A) | −2467 | 5080 | 1907 | 121 |
| H(12A) | −3484 | 1735 | 2054 | 101 |
| H(16A) | −5680 | 1062 | 2834 | 93 |
| H(17A) | −6134 | −662 | 1934 | 125 |
| H(18A) | −6127 | −647 | 371 | 124 |
| H(19A) | −8394 | 5775 | 610 | 130 |
| H(19B) | −8316 | 5530 | −420 | 130 |
| H(20A) | −8826 | 7086 | −933 | 199 |
| H(20B) | −9732 | 6417 | −673 | 199 |
| H(21A) | −8453 | 7911 | 416 | 293 |
| H(21B) | −9437 | 7269 | 594 | 293 |
| H(22A) | −10795 | 9011 | −483 | 376 |
| H(22B) | −10809 | 8090 | 173 | 376 |
| H(22C) | −9859 | 8973 | 526 | 376 |
| H(23A) | 4912 | 3972 | 3992 | 98 |
| H(26A) | 8366 | 5552 | 4551 | 101 |
| H(28A) | 6418 | 7185 | 5239 | 91 |
| H(31A) | 3702 | 4958 | 3175 | 118 |
| H(34A) | 4562 | 8330 | 3913 | 108 |
| H(36A) | 2462 | 10242 | 3291 | 330 |
| H(36B) | 1878 | 9578 | 2326 | 330 |
| H(36C) | 1523 | 9392 | 3251 | 330 |
| H(38A) | 6829 | 9019 | 6011 | 97 |
| H(39A) | 7286 | 10720 | 5419 | 140 |
| H(40A) | 7264 | 10682 | 3823 | 127 |
| H(45A) | 6224 | 6058 | 6911 | 106 |
| H(48A) | 2729 | 4447 | 5304 | 106 |
| H(53A) | 7509 | 5071 | 6887 | 116 |
| H(56A) | 6492 | 1710 | 7001 | 109 |
| H(58A) | 10892 | 1545 | 7484 | 816 |
| H(58B) | 10167 | 779 | 7888 | 816 |

TABLE 4-continued

Atomic coordinates (×10⁴) and equivalent isotropic displacement parameters ($Å^2 \times 10^3$) of the crystal of the compound of formula (II)

| | x | y | z | U(eq) |
|---|---|---|---|---|
| H(58C) | 9831 | 941 | 6759 | 816 |
| H(60A) | 4277 | 1087 | 7809 | 97 |
| H(61A) | 3906 | −664 | 6967 | 141 |
| H(62A) | 3930 | −665 | 5367 | 141 |
| H(67A) | −5115 | 3980 | −1040 | 93 |
| H(70A) | −1628 | 5608 | −446 | 101 |
| H(75A) | −6386 | 4968 | −1864 | 116 |
| H(78A) | −5344 | 8310 | −1063 | 105 |
| H(80A) | −7557 | 10264 | −1658 | 348 |
| H(80B) | −8091 | 9648 | −2659 | 348 |
| H(80C) | −8507 | 9400 | −1778 | 348 |
| H(82A) | −3172 | 9010 | 1033 | 95 |
| H(83A) | −2722 | 10707 | 373 | 159 |
| H(84A) | −2763 | 10713 | −1189 | 134 |

TABLE 5

Bond length (Å) and bond angle [deg] of the compound of formula (II)

| | | | |
|---|---|---|---|
| Cl(1)—C(2) | 1.70(2) | C(60)—C(59)—S(3) | 112.8(17) |
| Cl(2)—C(24) | 1.75(2) | C(50)—C(59)—S(3) | 126.8(18) |
| Cl(3)—C(46) | 1.765(19) | C(59)—C(60)—C(61) | 104(2) |
| Cl(4)—C(68) | 1.743(19) | C(59)—C(60)—H(60A) | 129.1 |
| S(1)—C(18) | 1.65(2) | C(16)—H(16A) | 0.93 |
| S(1)—C(15) | 1.70(2) | C(17)—C(18) | 1.29(3) |
| S(2)—C(37) | 1.67(2) | C(17)—H(17A) | 0.93 |
| S(2)—C(40) | 1.64(3) | C(18)—H(18A) | 0.93 |
| S(3)—C(62) | 1.65(2) | C(19)—C(20) | 1.52(3) |
| S(3)—C(59) | 1.70(2) | C(19)—H(19A) | 0.97 |
| S(4)—C(84) | 1.67(3) | C(19)—H(19B) | 0.97 |
| S(4)—C(81) | 1.65(2) | C(20)—C(21) | 1.26(5) |
| O(1)—C(3) | 1.40(2) | C(20)—H(20A) | 0.97 |
| O(1)—C(19) | 1.30(3) | C(20)—H(20B) | 0.97 |
| O(2)—C(5) | 1.40(2) | C(21)—H(21A) | 0.97 |
| O(2)—C(6) | 1.39(2) | C(21)—H(21B) | 0.97 |
| O(3)—C(10) | 1.25(3) | C(22)—H(22A) | 0.96 |
| O(4)—C(13) | 1.10(6) | C(22)—H(22B) | 0.96 |
| O(5)—C(13) | 1.40(6) | C(22)—H(22C) | 0.96 |
| O(5)—C(14) | 1.57(6) | C(23)—C(24) | 1.33(3) |
| O(6)—C(22) | 1-17(5) | C(23)—C(30) | 1.42(3) |
| O(6)—C(21) | 1.36(4) | C(23)—H(23A) | 0.93 |
| O(7)—C(25) | 1.37(3) | C(24)—C(25) | 1.33(3) |
| O(7)—C(41) | 1.49(3) | C(25)—C(26) | 1.43(3) |
| O(8)—C(27) | 1.38(2) | C(26)—C(27) | 1.37(3) |
| O(8)—C(28) | 1.44(2) | C(26)—H(26A) | 0.93 |
| O(9)—C(32) | 1.29(3) | C(27)—C(30) | 1.40(3) |
| O(10)—C(35) | 1.16(3) | C(28)—C(37) | 1.46(3) |
| O(11)—C(35) | 1.33(4) | C(28)—H(28A) | 0.98 |
| O(11)—C(36) | 1.40(4) | C(29)—C(31) | 1.31(3) |
| O(13)—C(47) | 1.36(3) | C(29)—C(30) | 1.42(3) |
| O(13)—C(63) | 1.43(3) | C(31)—C(32) | 1.43(4) |
| O(14)—C(49) | 1.38(2) | C(31)—H(31A) | 0.93 |
| O(14)—C(50) | 1.41(2) | C(32)—C(33) | 1.42(4) |
| O(15)—C(54) | 1.25(3) | C(33)—C(34) | 1.43(3) |
| O(16)—C(57) | 1.40(5) | C(33)—C(35) | 1.44(4) |
| O(16)—C(58) | 1.53(4) | C(34)—H(34A) | 0.93 |
| O(17)—C(57) | 1.10(6) | C(36)—H(36A) | 0.96 |
| O(18)—C(66) | 1.18(5) | C(36)—H(36B) | 0.96 |
| O(18)—C(65) | 1.37(4) | C(36)—H(36C) | 0.96 |
| O(19)—C(69) | 1.33(3) | C(37)—C(38) | 1.52(3) |
| O(19)—C(85) | 1.44(3) | C(38)—C(39) | 1.46(3) |
| O(20)—C(71) | 1.37(2) | C(38)—H(38A) | 0.93 |
| O(20)—C(72) | 1.41(2) | C(39)—C(40) | 1.30(3) |
| O(21)—C(76) | 1.31(3) | C(39)—H(39A) | 0.93 |
| O(22)—C(79) | 1.16(4) | C(40)—H(40A) | 0.93 |
| O(23)—C(79) | 1.33(5) | C(41)—C(42) | 1.81(6) |
| O(23)—C(80) | 1.42(3) | C(45)—C(46) | 1.39(3) |
| N(1)—C(12) | 1.37(2) | C(45)—C(52) | 1.38(3) |
| N(1)—C(7) | 1.38(2) | C(45)—H(45A) | 0.93 |
| N(1)—C(6) | 1.52(3) | C(46)—C(47) | 1.42(3) |
| N(2)—C(34) | 1.36(3) | C(47)—C(48) | 1.36(3) |
| N(2)—C(29) | 1.38(3) | C(48)—C(49) | 1.41(3) |
| N(2)—C(28) | 1.49(2) | C(48)—H(48A) | 0.93 |
| N(3)—C(56) | 1.38(2) | C(49)—C(52) | 1.37(3) |
| N(3)—C(51) | 1.39(2) | C(50)—C(59) | 1.48(3) |
| N(3)—C(50) | 1.52(2) | C(51)—C(53) | 1.36(3) |
| N(4)—C(78) | 1.33(3) | C(51)—C(52) | 1.49(3) |
| N(4)—C(73) | 1.39(2) | C(53)—C(54) | 1.39(4) |
| N(4)—C(72) | 1.51(3) | C(53)—H(53A) | 0.93 |
| C(1)—C(2) | 1.44(3) | C(54)—C(55) | 1.52(4) |
| C(1)—C(8) | 1.38(3) | C(55)—C(56) | 1.32(3) |
| C(1)—H(1A) | 0.93 | C(55)—C(57) | 1.60(4) |
| C(2)—C(3) | 1.38(3) | C(56)—H(56A) | 0.93 |
| C(3)—C(4) | 1.33(3) | C(58)—H(58A) | 0.96 |
| C(4)—C(5) | 1.36(3) | C(58)—H(58B) | 0.96 |
| C(4)—H(4A) | 0.93 | C(58)—H(58C) | 0.96 |
| C(5)—C(8) | 1.38(3) | C(59)—C(60) | 1.50(3) |
| C(6)—C(15) | 1.51(3) | C(60)—C(61) | 1.49(3) |
| C(6)—H(6A) | 0.98 | C(60)—H(60A) | 0.93 |
| C(7)—C(9) | 1.36(3) | C(61)—C(62) | 1.33(3) |
| C(7)—C(8) | 1.51(3) | C(61)—H(61A) | 0.93 |
| C(9)—C(10) | 1.40(4) | C(62)—H(62A) | 0.93 |
| C(9)—H(9A) | 0.93 | C(63)—C(64) | 1.58(3) |
| C(10)—C(11) | 1.48(3) | C(64)—C(65) | 1.32(5) |
| C(11)—C(12) | 1.32(3) | C(67)—C(68) | 1.32(3) |
| C(11)—C(13) | 1.67(5) | C(67)—C(74) | 1.40(3) |
| C(12)—H(12A) | 0.93 | C(67)—H(67A) | 0.93 |
| C(15)—C(16) | 1.49(3) | C(68)—C(69) | 1.35(3) |
| C(16)—C(17) | 1.48(3) | C(69)—C(70) | 1.43(3) |
| C(73)—C(75) | 1.34(3) | C(70)—C(71) | 1.37(3) |
| C(73)—C(74) | 1.41(3) | C(70)—H(70A) | 0.93 |
| C(75)—C(76) | 1.45(4) | C(71)—C(74) | 1.42(3) |
| C(75)—H(75A) | 0.93 | C(72)—C(81) | 1.49(3) |
| C(76)—C(77) | 1.46(4) | C(10)—C(9)—H(9A) | 118.7 |
| C(77)—C(78) | 1.39(3) | O(3)—C(10)—C(9) | 121(3) |
| C(77)—C(79) | 1.41(4) | O(3)—C(10)—C(11) | 123(3) |
| C(78)—H(78A) | 0.93 | C(9)—C(10)—C(11) | 116(3) |
| C(80)—H(80A) | 0.96 | C(12)—C(11)—C(10) | 118(3) |
| C(80)—H(80B) | 0.96 | C(12)—C(11)—C(13) | 109(3) |
| C(80)—H(80C) | 0.96 | C(10)—C(11)—C(13) | 133(3) |
| C(81)—C(82) | 1.51(3) | C(11)—C(12)—N(1) | 125(2) |
| C(82)—C(83) | 1.50(4) | C(11)—C(12)—H(12A) | 117.3 |
| C(82)—H(82A) | 0.93 | N(1)—C(12)—H(12A) | 118 |
| C(83)—C(84) | 1.26(4) | O(4)—C(13)—O(5) | 134(4) |
| C(83)—H(83A) | 0.93 | O(4)—C(13)—C(11) | 124(4) |
| C(84)—H(84A) | 0.93 | O(5)—C(13)—C(11) | 100(4) |
| C(85)—C(86) | 1.47(7) | C(6)—C(15)—C(16) | 123.8(18) |
| C(86)—C(87) | 1.39(7) | C(6)—C(15)—S(1) | 121.0(16) |
| C(88)—O(24) | 2.06(5) | C(16)—C(15)—S(1) | 115.1(14) |
| O(24)—C(87) | 2.10(7) | C(17)—C(16)—C(15) | 101.8(19) |
| C(18)—S(1)—C(15) | 90.0(12) | C(17)—C(16)—H(16A) | 129.6 |
| C(37)—S(2)—C(40) | 93.6(13) | C(15)—C(16)—H(16A) | 128.5 |
| C(62)—S(3)—C(59) | 92.8(13) | C(18)—C(17)—C(16) | 116(2) |
| C(84)—S(4)—C(81) | 93.4(14) | C(18)—C(17)—H(17A) | 122 |
| C(3)—O(1)—C(19) | 120.4(19) | C(16)—C(17)—H(17A) | 121.9 |
| C(5)—O(2)—C(6) | 114.7(15) | C(17)—C(18)—S(1) | 117.0(19) |
| C(13)—O(5)—C(14) | 104(4) | C(17)—C(18)—H(18A) | 121.9 |
| C(22)—O(6)—C(21) | 119(5) | S(1)—C(18)—H(18A) | 121.1 |
| C(25)—O(7)—C(41) | 127.4(19) | O(1)—C(19)—C(20) | 116(3) |
| C(27)—O(8)—C(28) | 111.7(15) | O(1)—C(19)—H(19A) | 108.5 |
| C(35)—O(11)—C(36) | 112(3) | C(20)—C(19)—H(19A) | 108 |
| C(47)—O(13)—C(63) | 115.4(18) | O(1)—C(19)—H(19B) | 108 |
| C(49)—O(14)—C(50) | 112.9(14) | C(20)—C(19)—H(19B) | 108.1 |
| C(57)—O(16)—C(58) | 112(4) | H(19A)—C(19)—H(19B) | 107.5 |
| C(66)—O(18)—C(65) | 121(4) | C(21)—C(20)—C(19) | 123(4) |
| C(69)—O(19)—C(85) | 118(2) | C(21)—C(20)—H(20A) | 108.8 |
| C(71)—O(20)—C(72) | 111.7(16) | C(19)—C(20)—H(20A) | 106 |
| C(79)—O(23)—C(80) | 111(3) | C(21)—C(20)—H(20B) | 104.3 |
| C(12)—N(1)—C(7) | 119.0(19) | C(19)—C(20)—H(20B) | 107.1 |
| C(12)—N(1)—C(6) | 123.5(19) | H(20A)—C(20)—H(20B) | 106.5 |
| C(7)—N(1)—C(6) | 117.1(16) | C(20)—C(21)—O(6) | 117(5) |
| C(34)—N(2)—C(29) | 122(2) | C(20)—C(21)—H(21A) | 106 |
| C(34)—N(2)—C(28) | 121(2) | O(6)—C(21)—H(21A) | 105.9 |
| C(29)—N(2)—C(28) | 116.2(17) | C(20)—C(21)—H(21B) | 110.6 |
| C(56)—N(3)—C(51) | 120.9(18) | O(6)—C(21)—H(21B) | 109.7 |
| C(56)—N(3)—C(50) | 121.2(18) | H(21A)—C(21)—H(21B) | 107.3 |
| C(51)—N(3)—C(50) | 117.3(15) | O(6)—C(22)—H(22A) | 110.4 |
| C(78)—N(4)—C(73) | 121.1(19) | O(6)—C(22)H—(22B) | 112.3 |
| C(78)—N(4)—C(72) | 120.2(18) | H(22A)—C(22)—H(22B) | 109.5 |

TABLE 5-continued

Bond length (Å) and bond angle [deg] of the compound of formula (II)

| | | | | | | | |
|---|---|---|---|---|---|---|---|
| C(73)—N(4)—C(72) | 118.2(16) | O(6)—C(22)—H(22C) | 105.6 | C(40)—C(39)—H(39A) | 122.9 | C(71)—C(70)—H(70A) | 122.2 |
| C(2)—C(1)—C(8) | 119(2) | H(22A)—C(22)—H(22C) | 109.5 | C(38)—C(39)—H(39A) | 122.5 | C(69)—C(70)—H(70A) | 121.1 |
| C(2)—C(1)—H(1A) | 120.4 | H(22B)—C(22)—H(22C) | 109.5 | C(39)—C(40)—S(2) | 116(2) | O(20)—C(71)—C(70) | 116.5(19) |
| C(8)—C(1)—H(1A) | 120.8 | C(24)—C(23)—C(30) | 122(2) | C(39)—C(40)—H(40A) | 122 | O(20)—C(71)—C(74) | 121.4(18) |
| C(1)—C(2)—C(3) | 117.1(19) | C(24)—C(23)—H(23A) | 119.1 | S(2)—C(40)—H(40A) | 122.4 | C(70)—C(71)—C(74) | 122(2) |
| C(1)—C(2)—Cl(1) | 120.0(17) | C(30)—C(23)—H(23A) | 118.6 | O(7)—C(41)—C(42) | 97(2) | O(20)—C(72)—N(4) | 107.3(16) |
| C(3)—C(2)—Cl(1) | 123(2) | C(23)—C(24)—C(25) | 124(2) | C(46)—C(45)—C(52) | 115(2) | O(20)—C(72)—C(81) | 106.2(18) |
| O(1)—C(3)—C(4) | 122(2) | C(23)—C(24)—Cl(2) | 119(2) | C(46)—C(45)—H(45A) | 122.3 | N(4)—C(72)—C(81) | 114.5(16) |
| O(1)—C(3)—C(2) | 113(2) | C(25)—C(24)—Cl(2) | 116(2) | C(52)—C(45)—H(45A) | 122.2 | C(75)—C(73)—N(4) | 119(2) |
| C(4)—C(3)—C(2) | 125(2) | C(24)—C(25)—O(7) | 123(2) | C(45)—C(46)—C(47) | 125.9(19) | C(75)—C(73)—C(74) | 125(2) |
| C(3)—C(4)—C(5) | 117(2) | C(24)—C(25)—C(26) | 117(2) | C(45)—C(46)—Cl(3) | 116.0(19) | N(4)—C(73)—C(74) | 116.9(18) |
| C(3)—C(4)—H(4A) | 121.7 | O(7)—C(25)—C(26) | 120(2) | C(47)—C(46)—Cl(3) | 118.1(17) | C(71)—C(74)—C(67) | 117(2) |
| C(5)—C(4)—H(4A) | 121.7 | C(27)—C(26)—C(25) | 120(2) | O(13)—C(47)—C(48) | 128(2) | C(71)—C(74)—C(73) | 117.1(18) |
| C(8)—C(5)—O(2) | 115.4(18) | C(27)—C(26)—H(26A) | 119.7 | O(13)—C(47)—C(46) | 118(2) | C(67)—C(74)—C(73) | 126.1(19) |
| C(8)—C(5)—C(4) | 124.2(19) | C(25)—C(26)—H(26A) | 120 | C(48)—C(47)—C(46) | 114(2) | C(73)—C(75)—C(76) | 123(3) |
| O(2)—C(5)—C(4) | 120.3(18) | O(8)—C(27)—C(26) | 118.9(19) | C(47)—C(48)—C(49) | 123(2) | C(73)—C(75)—H(75A) | 118.7 |
| O(2)—C(6)—C(15) | 110.8(17) | O(8)—C(27)—C(30) | 118.8(19) | C(47)—C(48)—H(48A) | 117.9 | C(76)—C(75)—H(75A) | 118.1 |
| O(2)—C(6)—N(1) | 108.3(16) | C(26)—C(27)—C(30) | 122(2) | C(49)—C(48)—H(48A) | 119.4 | O(21)—C(76)—C(75) | 119(3) |
| C(15)—C(6)—N(1) | 111.3(17) | O(8)—C(28)—C(37) | 106.3(17) | O(14)—C(49)—C(52) | 120.8(19) | O(21)—C(76)—C(77) | 124(3) |
| O(2)—C(6)—H(6A) | 108.9 | O(8)—C(28)—N(2) | 109.1(15) | O(14)—C(49)—C(48) | 119.8(19) | C(75)—C(76)—C(77) | 116(2) |
| C(15)—C(6)—H(6A) | 108.5 | C(37)—C(28)—N(2) | 116.3(17) | C(52)—C(49)—C(48) | 119(2) | C(78)—C(77)—C(79) | 127(3) |
| N(1)—C(6)—H(6A) | 108.9 | O(8)—C(28)—H(28A) | 108.1 | C(14)—C(50)—C(59) | 106.3(16) | C(78)—C(77)—C(76) | 116(3) |
| C(9)—C(7)—N(1) | 120(2) | C(37)—C(28)—H(28A) | 108.3 | O(14)—C(50)—N(3) | 105.0(16) | C(79)—C(77)—C(76) | 117(3) |
| C(9)—C(7)—C(8) | 126(2) | N(2)—C(28)—H(28A) | 108.5 | C(59)—C(50)—N(3) | 110.4(17) | N(4)—C(78)—C(77) | 125(2) |
| N(1)—C(7)—C(8) | 114.6(18) | C(31)—C(29)—N(2) | 118(2) | C(53)—C(51)—N(3) | 118(2) | N(4)—C(78)—H(78A) | 117.6 |
| C(5)—C(8)—C(1) | 118(2) | C(31)—C(29)C—(30) | 123(2) | C(53)—C(51)—C(52) | 126(2) | C(77)—C(78)—H(78A) | 117.8 |
| C(5)—C(8)—C(7) | 121.7(18) | N(2)—C(29)—C(30) | 119(2) | N(3)—C(51)—C(52) | 115.8(18) | O(22)C—(79)—O(23) | 113(4) |
| C(1)—C(8)—C(7) | 119.9(19) | C(29)—C(30)—C(27) | 119(2) | C(49)—C(52)—C(45) | 122(2) | O(22)—C(79)—C(77) | 137(5) |
| C(7)—C(9)—C(10) | 122(3) | C(29)—C(30)—C(23) | 127(2) | C(49)—C(52)—C(51) | 117(2) | O(23)—C(79)—C(77) | 109(4) |
| C(7)—C(9)—H(9A) | 118.8 | C(27)—C(30)—C(23) | 115(2) | C(45)—C(52)—C(51) | 121(2) | O(23)—C(80)—H(80A) | 109.5 |
| O(9)—C(32)—C(33) | 119(3) | C(29)—C(31)—C(32) | 127(3) | C(51)—C(53)—C(54) | 126(3) | O(23)—C(80)—H(80B) | 108.7 |
| C(31)—C(32)—C(33) | 113(3) | C(29)—C(31)—H(31A) | 116.7 | C(51)—C(53)—H(53A) | 116.9 | H(80A)—C(80)—H(80B) | 109.5 |
| C(34)—C(33)—C(35) | 116(3) | C(32)—C(31)—H(31A) | 116.7 | C(54)—C(53)—H(53A) | 116.7 | O(23)—C(80)—H(80C) | 110.2 |
| C(34)—C(33)—C(32) | 121(2) | O(9)—C(32)—C(31) | 128(3) | O(15)—C(54)—C(53) | 126(3) | H(80A)—C(80)—H(80C) | 109.5 |
| C(35)—C(33)—C(32) | 122(3) | C(61)—C(60)—H(60A) | 127.2 | O(15)—C(54)—C(55) | 122(3) | H(80B)—C(80)—H(80C) | 109.5 |
| N(2)—C(34)—C(33) | 118(2) | C(62)—C(61)—C(60) | 115(3) | C(53)—C(54)—C(55) | 112(2) | C(82)—C(81)—C(72) | 120(2) |
| N(2)—C(34)—H(34A) | 120.9 | C(62)—C(61)—H(61A) | 122.3 | C(56)—C(55)—C(54) | 122(2) | C(82)—C(81)—S(4) | 114.5(17) |
| C(33)—C(34)—H(34A) | 120.8 | C(60)—C(61)—H(61A) | 122.6 | C(56)—C(55)—C(57) | 108(3) | C(72)—C(81)—S(4) | 125.2(16) |
| O(10)—C(35)—O(11) | 110(3) | C(61)—C(62)—S(3) | 115(2) | C(54)—C(55)—C(57) | 131(3) | C(83)—C(82)—C(81) | 100(2) |
| O(10)—C(35)—C(33) | 136(3) | C(61)—C(62)—H(62A) | 122.1 | C(55)—C(56)—N(3) | 122(2) | C(83)—C(82)—H(82A) | 129.9 |
| O(11)—C(35)—C(33) | 114(3) | S(3)—C(62)—H(62A) | 122.6 | C(55)—C(56)—H(56A) | 118.5 | C(81)—C(82)—H(82A) | 130.3 |
| O(11)—C(36)—H(36A) | 110 | O(13)—C(63)—C(64) | 108(2) | N(3)—C(56)—H(56A) | 120 | C(84)—C(83)—C(82) | 120(3) |
| O(11)—C(36)—H(36B) | 109.1 | C(65)—C(64)—C(63) | 117(3) | O(17)—C(57)—O(16) | 126(3) | C(84)—C(83)—H(83A) | 120.1 |
| H(36A)—C(36)—H(36B) | 109.5 | C(64)—C(65)—O(18) | 113(5) | O(17)—C(57)—C(55) | 129(4) | C(82)—C(83)—H(83A) | 119.9 |
| O(11)—C(36)—H(36C) | 109.2 | C(68)—C(67)—C(74) | 123(2) | O(16)—C(57)—C(55) | 105(4) | C(83)—C(84)—S(4) | 112(3) |
| H(36A)—C(36)—H(36C) | 109.5 | C(68)—C(67)—H(67A) | 118.5 | O(16)—C(58)—H(58A) | 109.3 | C(83)—C(84)—H(84A) | 124 |
| H(36B)—C(36)—H(36C) | 109.5 | C(74)—C(67)—H(67A) | 118.9 | O(16)—C(58)—H(58B) | 104.4 | S(4)—C(84)—H(84A) | 123.7 |
| C(38)—C(37)—C(28) | 124(2) | C(67)—C(68)—C(69) | 121(2) | H(58A)—C(58)—H(58B) | 109.5 | O(19)—C(85)—C(86) | 123(4) |
| C(38)—C(37)—S(2) | 111.0(14) | C(67)—C(68)—Cl(4) | 121.6(19) | O(16)—C(58)—H(58C) | 114.6 | C(87)—C(86)—C(85) | 71(4) |
| C(28)—C(37)—S(2) | 125.2(18) | C(69)—C(68)—Cl(4) | 117.7(19) | H(58A)—C(58)—H(58C) | 109.5 | C(88)—O(24)—C(87) | 113(3) |
| C(39)—C(38)—C(37) | 105.2(19) | O(19)—C(69)—C(68) | 116(2) | H(58B)—C(58)—H(58C) | 109.5 | C(86)—C(87)—O(24) | 114(5) |
| C(39)—C(38)—H(38A) | 127.4 | O(19)—C(69)—C(70) | 123(2) | C(60)—C(59)—C(50) | 120(2) | | |
| C(37)—C(38)—H(38A) | 127.4 | C(68)—C(69)—C(70) | 121(2) | | | | |
| C(40)—C(39)—C(38) | 115(2) | C(71)—C(70)—C(69) | 117(2) | | | | |

TABLE 6

Twist angle [deg] of the compound of formula (II).

| | | | |
|---|---|---|---|
| C(8)—C(1)—C(2)—C(3) | 1(3) | C(52)—C(45)—C(46)—Cl(3) | −179.6(16) |
| C(8)—C(1)—C(2)—Cl(1) | −179.3(17) | C(63)—O(13)—C(47)—C(48) | 15(3) |
| C(19)—O(1)—C(3)—C(4) | 14(4) | C(63)—O(13)—C(47)—C(46) | −166(2) |
| C(19)—O(1)—C(3)—C(2) | −168(2) | C(45)—C(46)—C(47)—O(13) | −178(2) |
| C(1)—C(2)—C(3)—O(1) | −177.7(19) | Cl(3)—C(46)—C(47)—O(13) | 1(3) |
| Cl(1)—C(2)—C(3)—O(1) | 3(3) | C(45)—C(46)—C(47)—C(48) | 2(3) |
| C(1)—C(2)—C(3)—C(4) | 0(4) | Cl(3)—C(46)—C(47)—C(48) | −178.7(16) |
| Cl(1)—C(2)—C(3)—C(4) | 179.9(19) | O(13)—C(47)—C(48)—C(49) | 178(2) |
| O(1)—C(3)—C(4)—C(5) | 178(2) | C(46)—C(47)—C(48)—C(49) | −2(3) |
| C(2)—C(3)—C(4)—C(5) | 1(4) | C(50)—O(14)—C(49)—C(52) | 39(3) |
| C(6)—O(2)—C(5)—C(8) | 39(3) | C(50)—O(14)—C(49)—C(48) | −143(2) |
| C(6)—O(2)—C(5)—C(4) | −145(2) | C(47)—C(48)—C(49)—O(14) | −179(2) |
| C(3)—C(4)—C(5)—C(8) | −3(4) | C(47)—C(48)—C(49)—C(52) | 0(3) |
| C(3)—C(4)—C(5)—O(2) | −179(2) | C(49)—O(14)—C(50)—C(59) | −179.4(18) |
| C(5)—O(2)—C(6)—C(15) | 176.0(17) | C(49)—O(14)—C(50)—N(3) | −62(2) |
| C(5)—O(2)—C(6)—N(1) | −61.6(19) | C(56)—N(3)—C(50)—O(14) | −138.7(18) |
| C(12)—N(1)—C(6)—O(2) | −141.7(18) | C(51)—N(3)—C(50)—O(14) | 50(2) |

TABLE 6-continued

Twist angle [deg] of the compound of formula (II).

| | | | |
|---|---|---|---|
| C(7)—N(1)—C(6)—O(2) | 46(2) | C(56)—N(3)—C(50)—C(59) | −25(3) |
| C(12)—N(1)—C(6)—C(15) | −20(3) | C(51)—N(3)—C(50)—C(59) | 164.4(17) |
| C(7)—N(1)—C(6)C—(15) | 168.3(17) | C(56)—N(3)—C(51)—C(53) | 2(3) |
| C(12)—N(1)—C(7)—C(9) | 2(3) | C(50)—N(3)—C(51)—C(53) | 172.7(19) |
| C(6)—N(1)—C(7)—C(9) | 174(2) | C(56)—N(3)—C(51)—C(52) | 176.5(18) |
| C(12)—N(1)—C(7)—C(8) | 178.4(18) | C(50)—N(3)—C(51)—C(52) | −12(3) |
| C(6)—N(1)—C(7)—C(8) | −9(3) | O(14)—C(49)—C(52)—C(45) | −179(2) |
| O(2)—C(5)—C(8)—C(1) | 180.0(19) | C(48)—C(49)—C(52)—C(45) | 2(3) |
| C(4)—C(5)—C(8)—C(1) | 4(4) | O(14)—C(49)—C(52)—C(51) | 4(3) |
| O(2)—C(5)—C(8)—C(7) | 2(3) | C(48)—C(49)—C(52)—C(51) | −174.9(19) |
| C(4)—C(5)—C(8)—C(7) | −174(2) | C(46)—C(45)—C(52)—C(49) | −2(3) |
| C(2)—C(1)—C(8)—C(5) | −3(3) | C(46)—C(45)—C(52)—C(51) | 175.2(19) |
| C(2)—C(1)—C(8)—C(7) | 175.1(19) | C(53)—C(51)—C(52)—C(49) | 159(2) |
| C(9)—C(7)—C(8)—C(5) | 160(2) | N(3)—C(51)—C(52)—C(49) | −16(3) |
| N(1)—C(7)—C(8)—C(5) | −16(3) | C(53)—C(51)—C(52)—C(45) | −19(3) |
| C(9)—C(7)—C(8)—C(1) | −18(3) | N(3)—C(51)—C(52)—C(45) | 166.9(19) |
| N(1)—C(7)—C(8)—C(1) | 166(2) | N(3)—C(51)—C(53)—C(54) | −2(3) |
| N(1)—C(7)—C(9)—C(10) | −2(4) | C(52)—C(51)—C(53)—C(54) | −177(2) |
| C(8)—C(7)—C(9)—C(10) | −177(2) | C(51)—C(53)—C(54)—O(15) | −174(2) |
| C(7)—C(9)—C(10)—O(3) | −179(2) | C(51)—C(53)—C(54)—C(55) | 2(4) |
| C(7)—C(9)—C(10)—C(11) | 3(4) | O(15)—C(54)—C(55)—C(56) | 175(2) |
| O(3)—C(10)—C(11)—C(12) | 177(2) | C(53)—C(54)—C(55)—C(56) | −1(4) |
| C(9)—C(10)—C(11)—C(12) | −4(4) | O(15)—C(54)—C(55)—C(57) | −3(5) |
| O(3)—C(10)—C(11)—C(13) | −4(5) | C(53)—C(54)—C(55)—C(57) | −179(2) |
| C(9)—C(10)—C(11)—C(13) | 175(3) | C(54)—C(55)—C(56)—N(3) | 1(4) |
| C(10)—C(11)—C(12)—N(1) | 5(4) | C(57)—C(55)—C(56)—N(3) | 179(2) |
| C(13)—C(11)—C(12)—N(1) | −174(2) | C(51)—N(3)—C(56)—C(55) | −1(3) |
| C(7)—N(1)—C(12)—C(11) | −4(3) | C(50)—N(3)—C(56)—C(55) | −172(2) |
| C(6)—N(1)—C(12)—C(11) | −176(2) | C(58)—C(16)—C(57)—O(17) | 18(6) |
| C(14)—C(5)—C(13)—O(4) | 18(8) | C(58)—O(16)—C(57)—C(55) | −161(3) |
| C(14)—O(5)—C(13)—C(11) | −179(3) | C(56)—C(55)—C(57)—O(17) | −3(6) |
| C(12)—C(11)—C(13)—O(4) | −14(6) | C(54)—C(55)—C(57)—O(17) | 176(4) |
| C(10)—C(11)—C(13)—O(4) | 166(5) | C(56)—C(55)—C(57)—O(16) | 176(2) |
| C(12)—C(11)—C(13)—O(5) | −180(2) | C(54)—C(55)—C(57)—O(16) | −6(4) |
| C(10)—C(11)—C(13)—O(5) | 1(4) | O(14)—C(50)—C(59)—C(60) | −134.1(19) |
| O(2)—C(6)—C(15)—C(16) | −132(2) | N(3)—C(50)—C(59)—C(60) | 113(2) |
| N(1)—C(6)—C(15)—C(16) | 107(2) | O(14)—C(50)—C(59)—S(3) | 41(3) |
| O(2)—C(6)—C(15)—S(1) | 44(2) | N(3)—C(50)—C(59)—S(3) | −73(2) |
| N(1)—C(6)—C(15)—S(1) | −77(2) | C(62)—S(3)—C(59)—C(60) | −4.8(18) |
| C(18)—S(1)—C(15)—C(6) | −178(2) | C(62)—S(3)—C(59)—C(50) | 180(2) |
| C(18)—S(1)—C(15)—C(16) | −2.0(19) | C(50)—C(59)—C(60)—C(61) | −180(2) |
| C(6)—C(15)—C(16)—C(17) | 178(2) | S(3)—C(59)—C(60)—C(61) | 5(2) |
| S(1)—C(15)—C(16)—C(17) | 2(2) | C(59)—C(60)—C(61)—C(62) | −3(3) |
| C(15)—C(16)—C(17)—C(18) | −1(3) | C(60)—C(61)—C(62)—S(3) | −1(4) |
| C(16)—C(17)—C(18)—S(1) | −1(4) | C(59)—S(3)—C(62)—C(61) | 3(3) |
| C(15)—S(1)—C(18)—C(17) | 1(3) | C(47)—O(13)—C(63)—C(64) | −175(2) |
| C(3)—O(1)—C(19)—C(20) | −176(2) | O(13)—C(63)—C(64)—C(65) | −56(4) |
| O(1)—C(19)—C(20)—C(21) | −65(5) | C(63)—C(64)—C(65)—O(18) | 177(4) |
| C(19)—C(20)—C(21)—O(6) | 175(4) | C(66)—O(18)—C(65)—C(64) | 121(7) |
| C(22)—O(6)—C(21)—C(20) | 149(6) | C(74)—C(67)—C(68)—C(69) | 3(4) |
| C(30)—C(23)—C(24)—C(25) | 1(4) | C(74)—C(67)—C(68)—Cl(4) | 177.6(16) |
| C(30)—C(23)—C(24)—Cl(2) | 179.9(15) | C(85)—O(19)—C(69)—C(68) | 179(2) |
| C(23)—C(24)—C(25)—O(7) | 176(2) | C(85)—O(19)—C(69)—C(70) | 2(4) |
| Cl(2)—C(24)—C(25)—O(7) | −3(3) | C(67)—C(68)—C(69)—O(19) | 179(2) |
| C(23)—C(24)—C(25)—C(26) | 0(4) | Cl(4)—C(68)—C(69)—O(19) | 3(3) |
| Cl(2)—C(24)—C(25)—C(26) | −179.1(16) | C(67)—C(68)—C(69)—C(70) | −5(4) |
| C(41)—O(7)—C(25)—C(24) | −172(2) | Cl(4)—C(68)—C(69)—C(70) | −179.9(17) |
| C(41)—O(7)—C(25)—C(26) | 4(4) | O(19)—C(69)—C(70)—C(71) | −179(2) |
| C(24)—C(25)—C(26)—C(27) | 1(4) | C(68)—C(69)—C(70)—C(71) | 4(4) |
| O(7)—C(25)—C(26)—C(27) | −175(2) | C(72)—O(20)—C(71)—C(70) | −144(2) |
| C(28)—O(8)—C(27)—C(26) | −147(2) | C(72)—O(20)—C(71)—C(74) | 37(3) |
| C(28)—O(8)—C(27)—C(30) | 38(3) | C(69)—C(70)—C(71)—O(20) | 179.0(19) |
| C(25)—C(26)—C(27)—O(8) | −177.5(19) | C(69)—C(70)—C(71)—C(74) | −1(4) |
| C(25)—C(26)—C(27)—C(30) | −3(4) | C(71)—O(20)—C(72)—N(4) | −58(2) |
| C(27)—O(8)—C(28)—N(2) | 175.0(17) | C(71)—O(20)—C(72)—C(81) | 178.9(17) |
| C(27)—O(8)—C(28)—C(37) | −59(2) | C(78)—N(4)—C(72)—O(20) | −142.4(18) |
| C(34)—N(2)—C(28)—O(8) | −144.3(18) | C(73)—N(4)—C(72)—O(20) | 46(2) |
| C(29)—N(2)—C(28)—O(8) | 44(2) | C(78)—N(4)—C(72)—C(81) | −25(3) |
| C(34)—N(2)—C(28)—C(37) | −24(3) | C(73)—N(4)—C(72)—C(81) | 163.5(18) |
| C(29)—N(2)—C(28)—C(37) | 164.1(19) | C(78)—N(4)—C(73)—C(75) | 3(3) |
| C(34)—N(2)—C(29)—C(31) | 4(3) | C(72)—N(4)—C(73)—C(75) | 175.1(18) |
| C(28)—N(2)—C(29)—C(31) | 176(2) | C(78)—N(4)—C(73)—C(74) | −179.6(18) |
| C(34)—N(2)—C(29)—C(30) | −179.2(19) | C(72)—N(4)—C(73)—C(74) | −8(3) |
| C(28)—N(2)—C(29)—C(30) | −8(3) | O(20)—C(71)—C(74)—C(67) | 179.0(18) |
| C(31)—C(29)—C(30)—C(27) | 161(2) | C(70)—C(71)—C(74)—C(67) | −1(3) |
| N(2)—C(29)—C(30)—C(27) | −16(3) | O(20)—C(71)—C(74)—C(73) | 4(3) |
| C(31)—C(29)—C(30)—C(23) | −17(4) | C(70)—C(71)—C(74)—C(73) | −176(2) |
| N(2)—C(29)—C(30)—C(23) | 166.2(19) | C(68)—C(67)—C(74)—C(71) | 0(3) |

TABLE 6-continued

Twist angle [deg] of the compound of formula (II).

| | | | |
|---|---|---|---|
| O(8)—C(27)—C(30)—C(29) | 0(3) | C(68)—C(67)—C(74)—C(73) | 175(2) |
| C(26)—C(27)—C(30)—C(29) | −175(2) | C(75)—C(73)—C(74)—C(71) | 159(2) |
| O(8)—C(27)—C(30)—C(23) | 178.1(17) | N(4)—C(73)—C(74)—C(71) | −18(3) |
| C(26)—C(27)—C(30)—C(23) | 4(3) | C(75)—C(73)—C(74)—C(67) | −16(4) |
| C(24)—C(23)—C(30)—C(29) | 176(2) | N(4)—C(73)—C(74)—C(67) | 167.5(19) |
| C(24)—C(23)—C(30)—C(27) | −3(3) | N(4)—C(73)—C(75)—C(76) | −3(3) |
| N(2)—C(29)—C(31)—C(32) | −3(4) | C(74)—C(73)—C(75)—C(76) | −180(2) |
| C(30)—C(29)—C(31)—C(32) | −180(2) | C(73)—C(75)—C(76)—O(21) | −177(2) |
| C(29)—C(31)—C(32)—O(9) | −179(3) | C(73)—C(75)—C(76)—C(77) | 2(4) |
| C(29)—C(31)—C(32)—C(33) | 2(4) | O(21)—C(76)—C(77)—C(78) | 178(2) |
| O(9)—C(32)—C(33)—C(34) | 179(2) | C(75)—C(76)—C(77)—C(78) | −1(4) |
| C(31)—C(32)—C(33)—C(34) | −1(3) | O(21)—C(76)—C(77)—C(79) | −5(4) |
| O(9)—C(32)—C(33)—C(35) | −1(4) | C(75)—C(76)—C(77)—C(79) | 176(2) |
| C(31)—C(32)—C(33)—C(35) | 179(2) | C(73)—N(4)—C(78)—C(77) | −3(3) |
| C(29)—N(2)—C(34)—C(33) | −4(3) | C(72)—N(4)—C(78)—C(77) | −174(2) |
| C(28)—N(2)—C(34)—C(33) | −174.8(18) | C(79)—C(77)—C(78)—N(4) | −175(3) |
| C(35)—C(33)—C(34)—N(2) | −178(2) | C(76)—C(77)—C(78)—N(4) | 1(4) |
| C(32)—C(33)—C(34)—N(2) | 2(3) | C(80)—C(23)—C(79)—O(22) | −12(5) |
| C(36)—C(11)—C(35)—O(10) | −3(4) | C(80)—O(23)—C(79)—C(77) | 178(3) |
| C(36)—O(11)—C(35)—C(33) | 176(3) | C(78)—C(77)—C(79)—O(22) | −179(4) |
| C(34)—C(33)—C(35)—O(10) | 173(4) | C(76)—C(77)—C(79)—O(22) | 4(7) |
| C(32)—C(33)—C(35)—O(10) | −7(5) | C(78)—C(77)—C(79)—O(23) | −12(5) |
| C(34)—C(33)—C(35)—O(11) | −5(4) | C(76)—C(77)—C(79)—O(23) | 171(3) |
| C(32)—C(33)—C(35)—O(11) | 175(2) | O(20)—C(72)—C(81)—C(82) | −132.8(19) |
| O(8)—C(28)—C(37)—C(38) | −131.6(19) | N(4)—C(72)—C(81)—C(82) | 109(2) |
| N(2)—C(28)—C(37)—C(38) | 107(2) | O(20)—C(72)—C(81)—S(4) | 50(2) |
| O(8)—C(28)—C(37)—S(2) | 54(2) | N(4)—C(72)—C(81)—S(4) | −68(2) |
| N(2)—C(28)—C(37)—S(2) | −68(2) | C(84)—S(4)—C(81)—C(82) | 0.1(18) |
| C(40)—S(2)—C(37)—C(38) | 0.8(17) | C(84)—S(4)—C(81)—C(72) | 177.1(19) |
| C(40)—S(2)—C(37)—C(28) | 176(2) | C(72)—C(81)—C(82)—C(83) | −177.6(19) |
| C(28)—C(37)—C(38)—C(39) | −176(2) | S(4)—C(81)—C(82)—C(83) | 0(2) |
| S(2)—C(37)—C(38)—C(39) | −1(2) | C(81)—C(82)—C(83)—C(84) | 1(3) |
| C(37)—C(38)—C(39)—C(40) | 0(3) | C(82)—C(83)—C(84)—S(4) | −1(4) |
| C(38)—C(39)—C(40)—S(2) | 0(3) | C(81)—S(4)—C(84)—C(83) | 0(3) |
| C(37)—S(2)—C(40)—C(39) | −1(2) | C(69)—O(19)—C(85)—C(86) | 144(4) |
| C(25)—O(7)—C(41)—C(42) | 177(3) | O(19)—C(85)—C(86)—C(87) | 55(5) |
| C(52)—C(45)—C(46)—C(47) | 0(3) | C(85)—C(86)—C(87)—O(24) | −168(4) |

Experimental Example 1: In Vitro HBV Activity Test of the Compound of Formula (I)

Experiment Materials

1. Cell Lines: HepG2.2.15 Cells

HepG2.2.15 cell culture medium, DMEM/F12, Invitrogen-11330032; 10% serum, Invitrogen-10099141; 100 units/ml penicillin and 100 μg/ml streptomycin, Hyclone-SV30010; 1% non-essential amino acids, Invitrogen-11140050; 2 mm L-GLUTAMINE, Invitrogen-25030081; 300 μg/ml Geneticin, Invitrogen-10131027

2. Reagents:

Pancreatin (Invitrogen-25300062)
DPBS (Corning-21031CVR)
Dimethyl sulfoxide (Sigma-D2650-100 ML)
High-throughput DNA purification kit (QIAamp 96 DNA Blood Kit, Qiagen-51162)
Quantitative faststart universal probe reagent (FastStart Universal Probe Master, Roche-04914058001)
Hepatitis B surface antigen quantitative detection kit (Autobio, CL 0310)

3. Consumables and Instruments 96-well cell culture plate (Corning-3599)
$CO_2$ incubator (HERA-CELL-240)
Optical sealing film (ABI-4311971)
Quantitative PCR 96-well plate (Applied Biosystems-4306737)
Fluorescence quantitative PCR instrument (Applied Biosystems-7500 real time PCR system)

Experimental Method

1. HepG2.2.15 cells ($4 \times 10^4$ cells/well) were seeded to a 96-well plate and incubated overnight at 37° C., 5% $CO_2$.

2. On day 2, the compound was diluted to a total of 8 concentrations, with a 3-fold gradient dilution. The compounds at different concentrations were added to culture wells in duplicate. The final concentration of dimethyl sulfoxide in the culture medium was 0.5%. 10 μM ETV was used as 100% inhibition control; 0.5% dimethyl sulfoxide was used as a 0% inhibition control.

3. On day 5, the culture medium was replaced with a fresh culture medium containing the compound.

4. On day 8, the culture media in the culture wells were collected, and part of the samples were taken to measure the content of hepatitis B virus S antigen by ELISA; part of the samples were taken to extract DNA using a high-throughput DNA purification kit (Qiagen-51162).

5. The preparation of PCR reaction solution was shown in Table 7:

TABLE 7

Preparation of PCR reaction solution

| Item | Volume required to configure one well (µl) | Volume required to configure 80 wells (µl) |
| --- | --- | --- |
| Quantitative faststart universal probe reagent | 12.5 | 1000 |
| Forward primer (10 µmol) | 1 | 80 |
| Reverse primer (10 µmol) | 1 | 80 |
| Probe (10 µmol) | 0.5 | 40 |

Forward primer sequence: GTGTCTGCGGCGTTTTATCA

Reverse primer sequence: GACAAACGGGCAACATACCTT

Probe sequence:  5' + FAM + CCTCTKCATCCTGCTGCTATGCCTCATC + TAMRA-3'

6.1 15 µL of reaction mixed solution was added to each well of a 96-well PCR plate, and then 10 µL of sample DNA or HBV DNA standards was added to each well.

6.2 PCR reaction conditions involve heating at 95° C. for 10 minutes, followed by denaturation at 95° C. for 15 seconds and extension at 60° C. for 1 minute, for a total of 40 cycles.

6.3 Determination of the content of hepatitis B virus S antigen by ELISA involve respectively adding 50 µl of samples and standards to a reaction plate, and then adding 50 µL of enzyme conjugate to each well; shaking same to mix uniformly, and incubating at 37° C. for 60 minutes; washing the plate 5 times with a washing solution, adding 50 µL of luminescent substrate to each well, mixing uniformly, and reacting same in the dark at room temperature for 10 minutes; and finally, detecting chemiluminescence intensity with a microplate reader.

6.4 Data analysis:

calculating percent inhibition: % Inh.=(1-value in sample/dimethyl sulfoxide control value)×100.

calculating $EC_{50}$: 50% inhibitory concentration ($EC_{50}$) value of the compound against HBV was calculated using GraphPad Prism software.

Experimental results are as shown in Table 8.

TABLE 8

In vitro activity test results

| Example | HBV-DNA $EC_{50}$ (nM) | HBsAg $EC_{50}$ (nM) |
| --- | --- | --- |
| Compound of formula (I) | 1.13 | 1.54 |

Experimental conclusion: the compound of formula (I) can effectively inhibit HBV-DNA and hepatitis B surface antigen (HBsAg).

What is claimed is:

1. A crystal form A of a compound of formula (I), wherein the crystal form has an X-ray powder diffraction pattern comprising characteristic diffraction peaks at the following 2θ angles: 6.30±0.20°, 9.30±0.20°, 9.84±0.20°, 18.68±0.20°, 20.16±0.20°, 23.06±0.20°, 24.00±0.20°, and 25.38±0.20°;

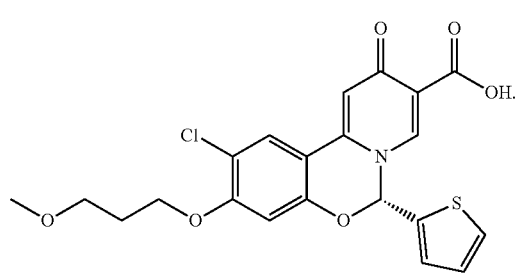

2. The crystal form A according to claim 1, wherein the crystal form has an X-ray powder diffraction pattern comprising characteristic diffraction peaks at the following 2θ angles: 6.30±0.20°, 9.30±0.20°, 9.84±0.20°, 12.84±0.20°, 18.68±0.20°, 20.16±0.20°, 21.26±0.20°, 23.06±0.20°, 24.00±0.20°, and 25.38±0.20°.

3. The crystal form A according to claim 2, wherein the crystal form has an X-ray powder diffraction pattern comprising characteristic diffraction peaks at the following 2θ angles: 6.302°, 7.883°, 9.301°, 9.842°, 12.838°, 15.436°, 16.580°, 18.124°, 18.680°, 19.459°, 20.161°, 20.800°, 21.262°, 21.704°, 23.057°, 24.000°, 24.837°, 25.382°, 26.244°, 26.558°, 27.740°, 28.119°, 28.827°, 29.502°, 29.880°, 30.261°, 30.762°, 31.678°, 32.595°, 33.061°, 34.347°, 35.235°, 35.738°, 36.642°, 38.619°, and 39.558°.

4. The crystal form A according to claim 3, wherein the crystal form has an XRPD pattern as shown in FIG. 1.

5. The crystal form A according to claim 1, wherein the crystal form has a differential scanning calorimetry profile comprising an endothermic peak at 224.58° C.±3° C.

Figure 2:
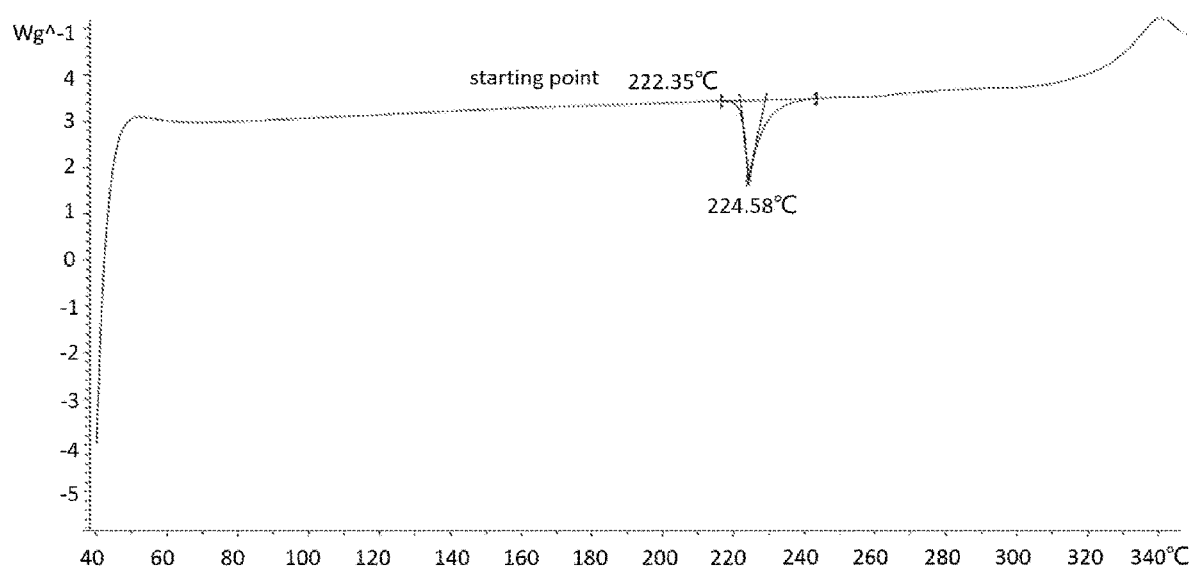
FIG. 2 is a DSC pattern of crystal form A of the compound of formula (I).

6. The crystal form A according to claim 5, wherein the crystal form has a DSC pattern as shown in FIG. 2.

7. The crystal form A according to claim 1, wherein the crystal form has a thermogravimetric analysis curve showing a weight loss of 0.127% at 200.00° C.±3° C. and a weight loss of 0.224% at 250° C.±3° C.

Figure 3:
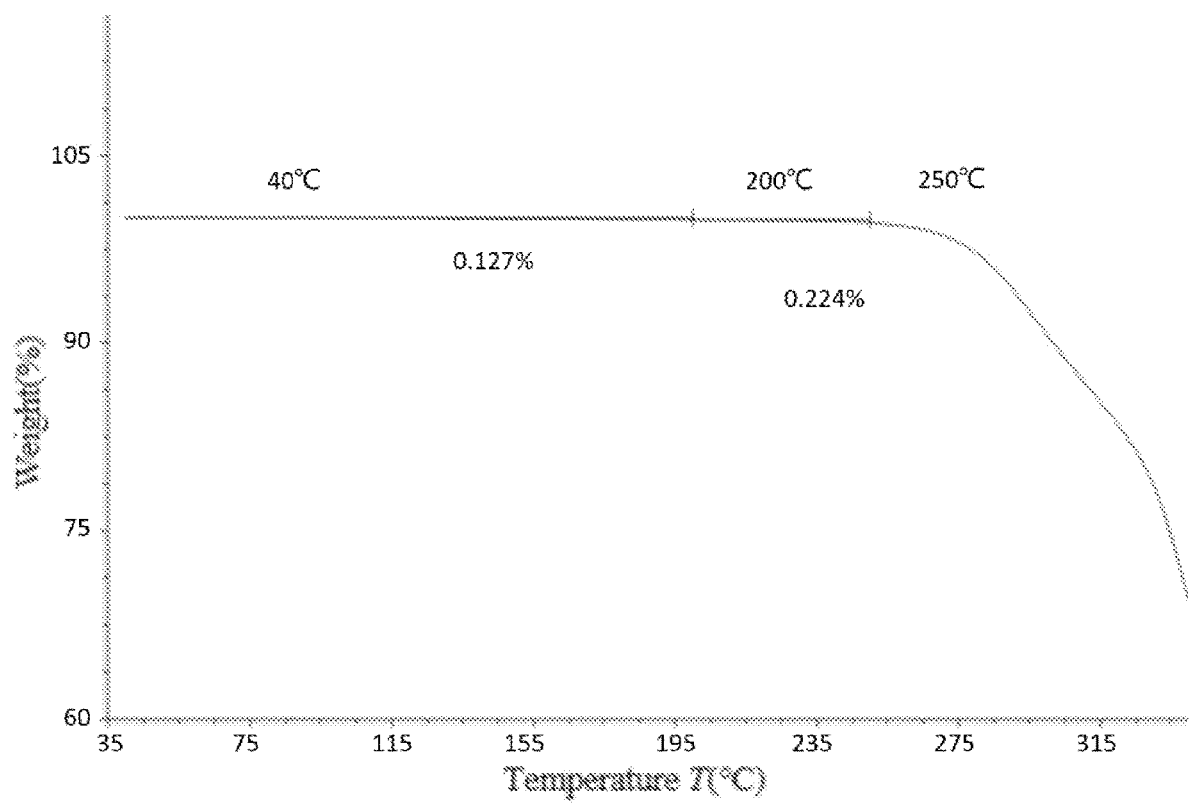
FIG. 3 is a TGA pattern of crystal form A of the compound of formula (I).

8. The crystal form A according to claim 7, wherein the crystal form has a TGA pattern as shown in FIG. 3.

9. A preparation method of the crystal form A of the compound of formula (I) as defined in claim 1, wherein the method comprises adding the compound of formula (I) in any form to an alcohol solvent, acetone, ethyl acetate, and acetonitrile, or an alcohol solvent, acetone, acetonitrile, and water, stirring the mixture for a given time at a given temperature, then filtering, and drying a filter cake to obtain the crystal form A.

10. The preparation method according to claim 9, wherein the volume ratio of the alcohol solvent, acetone, acetonitrile, and water is selected from 1:1-3.

11. The preparation method according to claim 9, wherein the alcohol solvent is selected from methanol, ethanol, or isopropanol.

12. The preparation method according to claim 9, wherein stirring is performed at a temperature selected from 25° C. to 65° C.

13. The preparation method according to claim 9, wherein stirring is performed for a time period selected from 1 hour to 72 hours.

14. The preparation method according to claim 9, wherein the weight ratio of the compound of formula (I) to the solvent is selected from 1:1-30.

* * * * *